United States Patent
Zhao et al.

(10) Patent No.: US 12,236,602 B2
(45) Date of Patent: Feb. 25, 2025

(54) SYSTEMS AND METHODS FOR USING REGISTERED FLUOROSCOPIC IMAGES IN IMAGE-GUIDED SURGERY

(71) Applicant: INTUITIVE SURGICAL OPERATIONS, INC., Sunnyvale, CA (US)

(72) Inventors: Tao Zhao, Sunnyvale, CA (US); Federico Barbagli, San Francisco, CA (US); Caitlin Q. Donhowe, Mountain View, CA (US); Vincent Duindam, San Francisco, CA (US); Michael D. Paris, San Francisco, CA (US); Timothy D. Soper, San Jose, CA (US); Oliver J. Wagner, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/652,927

(22) Filed: May 2, 2024

(65) Prior Publication Data

US 2024/0281976 A1 Aug. 22, 2024

Related U.S. Application Data

(63) Continuation of application No. 18/184,499, filed on Mar. 15, 2023, which is a continuation of application
(Continued)

(51) Int. Cl.
*G06T 7/00* (2017.01)
*A61B 6/00* (2006.01)
(Continued)

(52) U.S. Cl.
CPC .............. *G06T 7/0014* (2013.01); *A61B 6/12* (2013.01); *A61B 6/487* (2013.01); *A61B 6/5235* (2013.01);
(Continued)

(58) Field of Classification Search
CPC ................. G06T 7/0014; G06T 11/003; G06T 2207/30004; G06T 2207/1006;
(Continued)

(56) References Cited

U.S. PATENT DOCUMENTS 6,149,592 A 11/2000 Yanof et al.
6,380,732 B1 4/2002 Gilboa
(Continued)

FOREIGN PATENT DOCUMENTS

CN 101524279 A 9/2009
CN 101809618 A 8/2010
(Continued)

OTHER PUBLICATIONS

Extended European Search Report for Application No. EP24159458. 9, mailed on May 22, 2024, 10 pages.
(Continued)

*Primary Examiner* — Ming Y Hon
(74) *Attorney, Agent, or Firm* — Haynes & Boone, LLP.

(57) ABSTRACT

A method performed by a computing system comprises receiving a fluoroscopic image of a patient anatomy while a portion of a medical instrument is positioned within the patient anatomy. The fluoroscopic image has a fluoroscopic frame of reference. The portion has a sensed position in an anatomic model frame of reference. The method further comprises identifying the portion in the fluoroscopic image and identifying an extracted position of the portion in the fluoroscopic frame of reference using the identified portion in the fluoroscopic image. The method further comprises
(Continued)

registering the fluoroscopic frame of reference to the anatomic model frame of reference based on the sensed position of the portion and the extracted position of the portion.

30 Claims, 13 Drawing Sheets

Related U.S. Application Data

No. 16/950,980, filed on Nov. 18, 2020, now Pat. No. 11,636,597, which is a continuation of application No. 16/076,290, filed as application No. PCT/US2017/017433 on Feb. 10, 2017, now Pat. No. 10,896,506.

(60) Provisional application No. 62/294,870, filed on Feb. 12, 2016, provisional application No. 62/294,879, filed on Feb. 12, 2016.

(51) Int. Cl.
　　*A61B 6/12* 　　(2006.01)
　　*A61B 34/10* 　　(2016.01)
　　*A61B 34/20* 　　(2016.01)
　　*G06T 11/00* 　　(2006.01)
　　*A61B 90/00* 　　(2016.01)

(52) U.S. Cl.
CPC .............. *A61B 34/10* (2016.02); *A61B 34/20* (2016.02); *G06T 11/003* (2013.01); *A61B 6/5247* (2013.01); *A61B 2034/105* (2016.02); *A61B 2034/2046* (2016.02); *A61B 2034/2061* (2016.02); *A61B 2034/2065* (2016.02); *A61B 2090/3762* (2016.02); *G06T 2207/10064* (2013.01); *G06T 2207/10072* (2013.01); *G06T 2207/30004* (2013.01)

(58) Field of Classification Search
CPC ........ G06T 2207/10072; A61B 6/5235; A61B 6/487; A61B 6/12; A61B 34/20; A61B 2090/3762; A61B 6/5247; A61B 2034/2065
See application file for complete search history.

(56) References Cited

U.S. PATENT DOCUMENTS

| | | | |
|---|---|---|---|
| 6,389,187 B1 | 5/2002 | Greenaway et al. | |
| 7,316,681 B2 | 1/2008 | Madhani et al. | |
| 7,772,541 B2 | 8/2010 | Froggatt et al. | |
| 8,494,613 B2* | 7/2013 | Markowitz ............ | A61B 90/13 600/117 |
| 8,900,131 B2 | 12/2014 | Chopra et al. | |
| 9,259,274 B2 | 2/2016 | Prisco | |
| 9,452,276 B2 | 9/2016 | Duindam et al. | |
| 9,592,095 B2 | 3/2017 | Panescu et al. | |
| 10,706,543 B2 | 7/2020 | Donhowe et al. | |
| 10,842,575 B2 | 11/2020 | Panescu et al. | |
| 10,896,506 B2 | 1/2021 | Zhao et al. | |
| 11,202,680 B2 | 12/2021 | Donhowe et al. | |
| 11,278,354 B2 | 3/2022 | Duindam et al. | |
| 11,298,116 B2* | 4/2022 | Brown ............... | A61B 17/0057 |
| 11,636,597 B2 | 4/2023 | Zhao et al. | |
| 11,666,397 B2 | 6/2023 | Panescu et al. | |
| 2004/0097805 A1 | 5/2004 | Verard et al. | |
| 2006/0013523 A1 | 1/2006 | Childers et al. | |
| 2007/0293721 A1 | 12/2007 | Gilboa | |
| 2008/0262342 A1 | 10/2008 | Averbruch | |
| 2008/0262812 A1* | 10/2008 | Arata ..................... | A61B 90/36 703/11 |
| 2009/0179914 A1 | 7/2009 | Dahlke | |
| 2010/0172556 A1* | 7/2010 | Cohen ................ | A61B 18/1492 600/407 |
| 2010/0217117 A1 | 8/2010 | Glossop et al. | |
| 2010/0296723 A1 | 11/2010 | Greer et al. | |
| 2011/0054308 A1* | 3/2011 | Cohen .................... | A61B 6/469 600/424 |
| 2011/0082367 A1* | 4/2011 | Regazzoni ............. | A61B 34/20 600/425 |
| 2011/0098553 A1 | 4/2011 | Robbins et al. | |
| 2011/0141140 A1 | 6/2011 | Duhamel et al. | |
| 2012/0065481 A1 | 3/2012 | Hunter et al. | |
| 2013/0072787 A1* | 3/2013 | Wallace ................ | A61B 90/50 600/424 |
| 2013/0216025 A1 | 8/2013 | Chan et al. | |
| 2014/0111541 A1* | 4/2014 | Tolkowsky ......... | A61B 17/1204 345/632 |
| 2014/0275985 A1* | 9/2014 | Walker ................... | A61B 5/062 606/130 |
| 2014/0276937 A1 | 9/2014 | Wong et al. | |
| 2014/0334709 A1* | 11/2014 | Siewerdsen ............... | G06T 7/32 382/132 |
| 2014/0369584 A1 | 12/2014 | Fan et al. | |
| 2015/0005865 A1 | 1/2015 | Bergman et al. | |
| 2015/0078516 A1* | 3/2015 | Ohashi ................. | A61B 6/4042 378/42 |
| 2015/0141764 A1* | 5/2015 | Harks ................ | A61B 5/02158 600/478 |
| 2015/0193946 A1* | 7/2015 | Wong ....................... | G06T 7/248 382/103 |
| 2015/0294082 A1* | 10/2015 | Passerini ................ | G16H 50/50 703/11 |
| 2016/0000302 A1 | 1/2016 | Brown et al. | |
| 2016/0005168 A1 | 1/2016 | Merlet | |
| 2016/0100909 A1* | 4/2016 | Wollowick ............ | G16H 40/63 600/424 |
| 2016/0302747 A1* | 10/2016 | Averbuch ............ | A61B 6/5235 |
| 2016/0317119 A1* | 11/2016 | Tahmasebi Maraghoosh ............. | A61B 8/085 |
| 2017/0007334 A1* | 1/2017 | Crawford ............... | A61B 34/30 |
| 2017/0014108 A1 | 1/2017 | Mazurowski | |
| 2017/0020628 A1 | 1/2017 | Averbuch | |
| 2017/0079719 A1* | 3/2017 | Warner .................. | G16H 50/50 |
| 2017/0151027 A1* | 6/2017 | Walker ................... | A61B 34/37 |
| 2017/0209071 A1* | 7/2017 | Zhao ........................ | G06T 7/149 |
| 2017/0258418 A1 | 9/2017 | Averbuch et al. | |
| 2018/0008222 A1* | 1/2018 | Chen ......................... | G06T 7/73 |
| 2018/0035966 A1 | 2/2018 | Merlet et al. | |
| 2018/0042544 A1* | 2/2018 | Graham ............... | A61B 5/6898 |
| 2018/0263706 A1 | 9/2018 | Averbuch | |
| 2020/0315562 A1 | 10/2020 | Weingarten et al. | |
| 2023/0215007 A1 | 7/2023 | Zhao et al. | |
| 2023/0372039 A1 | 11/2023 | Panescu et al. | |

FOREIGN PATENT DOCUMENTS

| | | |
|---|---|---|
| CN | 102711650 A | 10/2012 |
| CN | 103379861 A | 10/2013 |
| CN | 103767683 A | 5/2014 |
| CN | 104023629 A | 9/2014 |
| CN | 104274245 A | 1/2015 |
| CN | 105232152 A | 1/2016 |
| EP | 1421913 A1 | 5/2004 |
| EP | 1504726 A1 | 2/2005 |
| EP | 2963616 A2 | 1/2016 |
| JP | 2006110351 A | 4/2006 |
| JP | 2009519083 A | 5/2009 |
| JP | 2014059887 A | 4/2014 |
| WO | WO-2005073917 A2 | 8/2005 |
| WO | WO-2007047782 A2 | 4/2007 |
| WO | WO-2007069168 A2 | 6/2007 |
| WO | WO-2007095637 A1 | 8/2007 |
| WO | WO-2011086431 A1 | 7/2011 |
| WO | WO-2011100124 A1 | 8/2011 |
| WO | WO-2012052929 A2 | 4/2012 |
| WO | WO-2013001388 A1 | 1/2013 |
| WO | WO-2014106253 A1 | 7/2014 |
| WO | WO-2014186715 A1 | 11/2014 |
| WO | WO-2016018646 A1 | 2/2016 |

(56) References Cited

FOREIGN PATENT DOCUMENTS

OTHER PUBLICATIONS

Anonymous: "Basic Physics of Digital Radiography/The Applications—Wikibooks, Open Books for an Open World," Apr. 22, 2013, XP055937792, Retrieved from the Internet: URL:https://en.wikibooks.org/w/index.php?title=Basic_Physics_of_Digital_Radiography/The_Applications&oldid=2515134, 15pgs.

Carl J., et al., "A New Fiducial Marker for Image-guidedradiotherapy of Prostate Cancer: Clinical Experience," Acta Oncologica, Jan. 1, 2008, vol. 47 (7), pp. 1358-1366.

Co-pending U.S. Appl. No. 18/441,902, inventors Panescu; Dorin et al., filed Feb. 14, 2024.

Co-pending U.S. Appl. No. 18/441,965, inventors Panescu; Dorin et al., filed Feb. 14, 2024.

Extended European Search Report for Application No. 17750857.9 mailed on Aug. 7, 2019, 12 pages.

Extended European Search Report for Application No. EP22168838, mailed on Jul. 12, 2022, 10 pages.

International Preliminary Report on Patentability for Application No. PCT/US2017/017433, mailed on Aug. 14, 2018, 10 pages.

International Search Report and Written Opinion for Application No. PCT/US2017/017433, mailed on May 19, 2017, 12 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

| LANDMARK | FLUORO FRAME POSITION | MODEL FRAME POSITION |
|---|---|---|
| LANDMARK POINT A | $X_{FA}, Y_{FA}, Z_{FA}$ | $X_{MA}, Y_{MA}, Z_{MA}$ |
| LANDMARK POINT B | $X_{FB}, Y_{FB}, Z_{FB}$ | $X_{MB}, Y_{MB}, Z_{MB}$ |
| LANDMARK POINT C | $X_{FC}, Y_{FC}, Z_{FC}$ | $X_{MC}, Y_{MC}, Z_{MC}$ |

SYSTEMS AND METHODS FOR USING REGISTERED FLUOROSCOPIC IMAGES IN IMAGE-GUIDED SURGERY

RELATED APPLICATIONS

This patent application is a continuation of U.S. patent application Ser. No. 18/184,499, filed Mar. 15, 2023 which is a continuation of U.S. patent application Ser. No. 16/950, 980, filed Nov. 18, 2020 which is a continuation of U.S. patent application Ser. No. 16/076,290, filed Aug. 7, 2018 which is the U.S. national phase of International Application No. PCT/US2017/017433, filed Feb. 10, 2017, which designated the U.S. and claims priority to and the benefit of the filing date of U.S. Provisional Patent Application No. 62/294,870, entitled "SYSTEMS AND METHODS FOR USING FLUOROSCOPY TO ASSIST INSTRUMENT NAVIGATION IN IMAGE-GUIDED SURGERY," filed Feb. 12, 2016, and U.S. Provisional Patent Application No. 62/294,879 entitled "SYSTEMS AND METHODS FOR USING REGISTERED FLUOROSCOPIC IMAGES IN IMAGE-GUIDED SURGERY," filed Feb. 12, 2016, all of which are hereby incorporated by reference in their entirety.

FIELD

The present disclosure is directed to systems and methods for conducting an image-guided procedure, and more particularly to systems and methods for using registered real-time fluoroscopic images and prior-time anatomic images during an image-guided procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. To assist with reaching the target tissue location, the location and movement of the medical instruments may be correlated with pre-operative or prior intra-operative static images of the patient anatomy. With the image-guided instruments correlated to the images, the instruments may navigate natural or surgically created passageways in anatomic systems such as the lungs, the colon, the intestines, the kidneys, the heart, the circulatory system, or the like. Traditionally the pre-operative or intra-operative images of the patient anatomy are detailed, often three-dimensional, images. However, they are static prior-time representations of the patient anatomy. Fluoroscopy is an imaging modality that provides real-time images of the patient anatomy including any radiopaque instruments in use during a medical procedure on the patient anatomy. Fluoroscopic images, however, may not capture high quality images of certain types of tissues. Systems and methods are needed to register real-time fluoroscopic and prior-time static images to provide enhanced navigation information for performing image-guided surgery.

SUMMARY

The embodiments of the invention are summarized by the claims that follow the description.

In one embodiment, method performed by a computing system comprises receiving a fluoroscopic image of a patient anatomy while a portion of a medical instrument is positioned within the patient anatomy. The fluoroscopic image has a fluoroscopic frame of reference. This portion may be referred to as an indicator portion, and the portion may comprise any length of the medical instrument, including, by way of non-limiting example, a proximal section, a midsection, a distal section, and/or a distal end of the medical instrument. The portion has a sensed or otherwise known position in an anatomic model frame of reference. The method further comprises identifying the portion position in the fluoroscopic image and identifying an extracted position of the portion in the fluoroscopic frame of reference using the portion position in the fluoroscopic image. The method further comprises registering the fluoroscopic frame of reference to the anatomic model frame of reference based on the sensed position of the portion and the extracted position of the portion.

In another embodiment, a method performed by a computing system comprises identifying a set of positions of plurality of anatomic landmarks, the plurality of anatomic landmarks rendered in an anatomic model of passageways of a patient anatomy in a model frame of reference and receiving fluoroscopic image data of the patient anatomy while a portion of a medical instrument traverses the plurality of anatomic landmarks in the passageways of the patient anatomy. The fluoroscopic image data has a fluoroscopic frame of reference. The method further comprises identifying a set of portion positions at the plurality of anatomic landmarks in the fluoroscopic frame of reference and registering the set of positions of plurality of anatomic landmarks in the model frame of reference and the set of portion positions in the fluoroscopic frame of reference to a common frame of reference.

In another embodiment, a method performed by a computing system comprises receiving a set of model points for an anatomic model of passageways of a patient anatomy in a model frame of reference and receiving fluoroscopic image data of the patient anatomy while an indicator portion of a medical instrument traverses the passageways of the patient anatomy. The fluoroscopic image data has a fluoroscopic frame of reference. The method further comprises identifying from the fluoroscopic image data, a set of indicator portion position points in the fluoroscopic frame of reference and matching each indicator portion position point to a model point in the set of model points to generate a set of matches. The method further comprises registering the model frame of reference to the fluoroscopic frame of reference based on the set of matches.

In another embodiment, a computer-assisted medical system comprises a fluoroscopic imager having a plane of orientation within a surgical coordinate space, and one or more processors. The one or more processors are configured to perform a method including: receiving a fluoroscopic image of a patient anatomy while a portion of a medical instrument is positioned at a location within the patient anatomy, the fluoroscopic image having a plane of orientation. The method also comprises receiving a command to drive motion of the portion of the medical instrument, constraining actuation of the portion such that actuated movement of the portion is constrained to the plane of orientation of the fluoroscopic image, and driving the motion of the portion with the constrained actuation. In one aspect, system further comprises receiving sensor information from the medical instrument while driving the motion of the portion with the constrained actuation, recognizing movement of the portion out of the plane of orientation of the fluoroscopic image from the received sensor information, and receiving a signal to adjust the portion into the plane of orientation of the fluoroscopic image.

In another embodiment, a method performed by a computing system comprises receiving an anatomic model of a patient anatomy, wherein an area of interest is identified in the anatomic model. The method further comprises receiving shape sensor data from an instrument shape sensor of an instrument positioned within the patient anatomy and registered to the anatomic model, and determining a fluoroscopic image plane for display based on the received shape sensor data and the area of interest.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 9A:
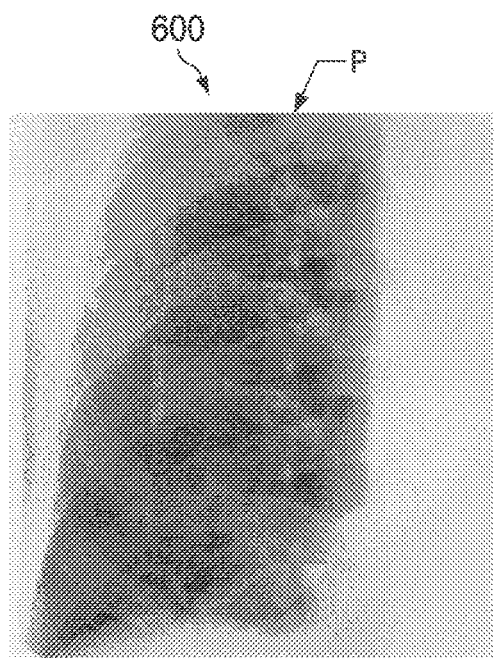
Figure 9B:
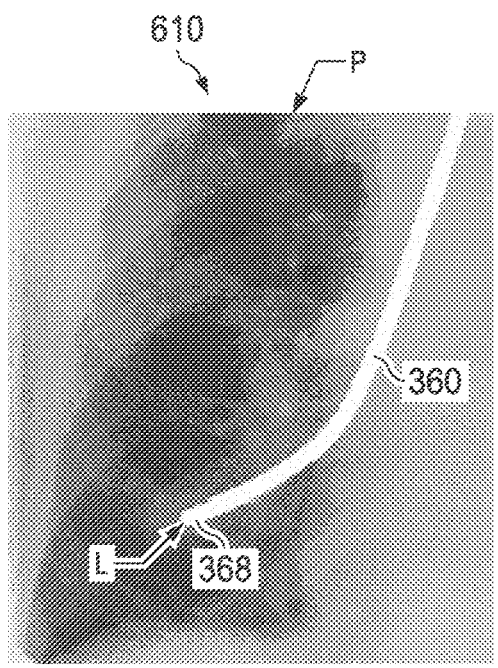
Figure 9C:
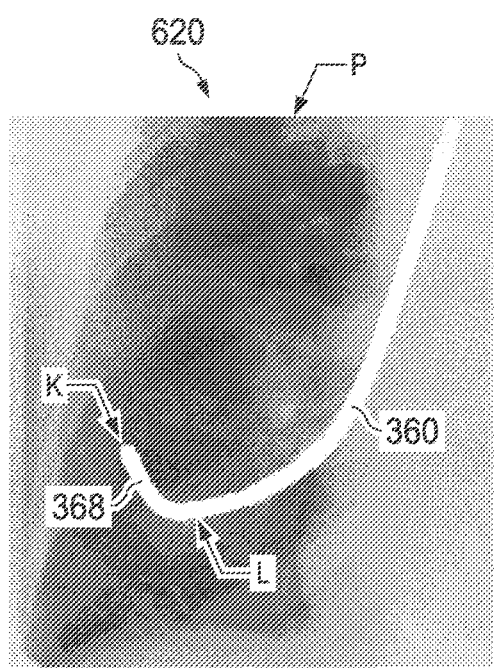

FIGS. 9A, 9B, and 9C illustrate fluoroscopic images for determining an instrument portion position in a fluoroscopic frame of reference.

Figure 10:
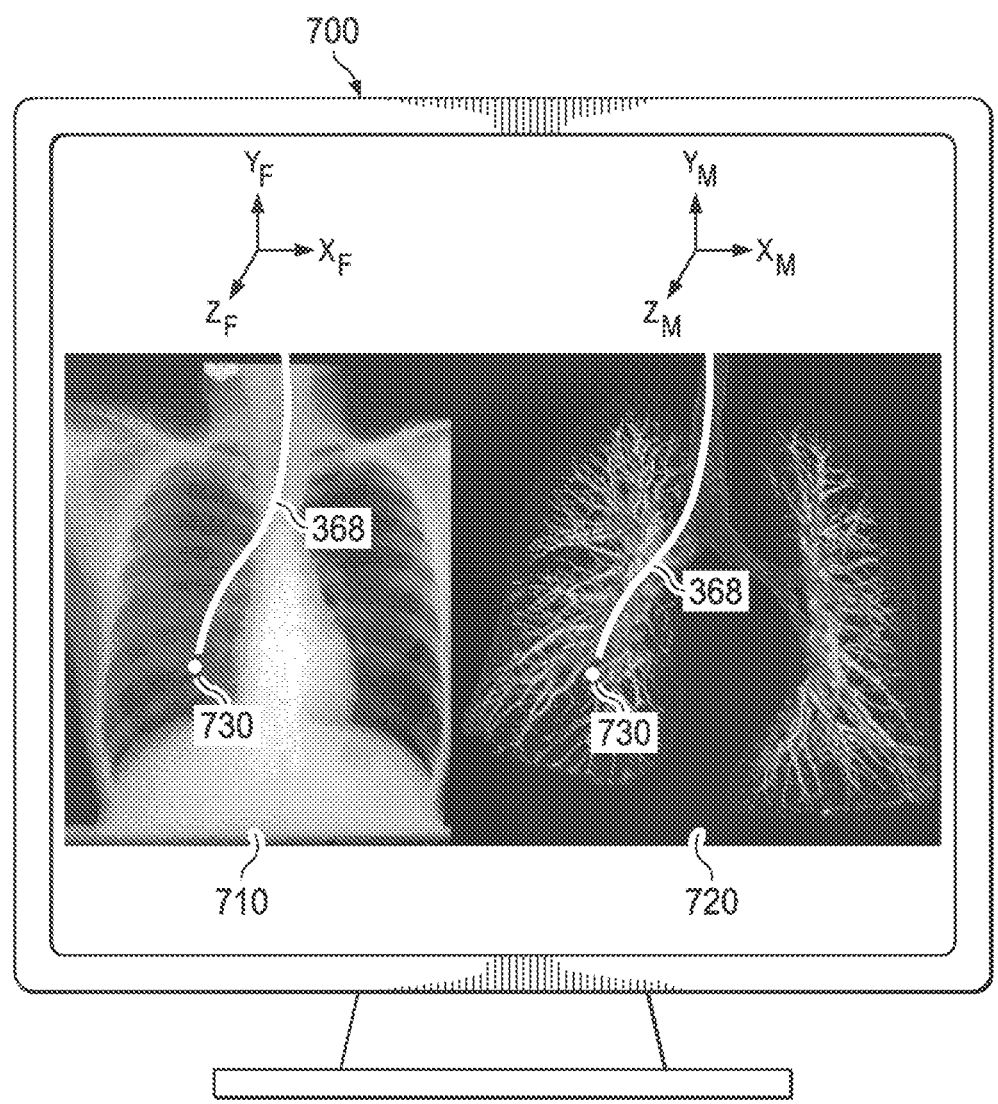

FIG. 10 is a display device on which is displayed registered side-by-side fluoroscopic and anatomic model images according to an embodiment of the present disclosure.

Figures 11, 12:
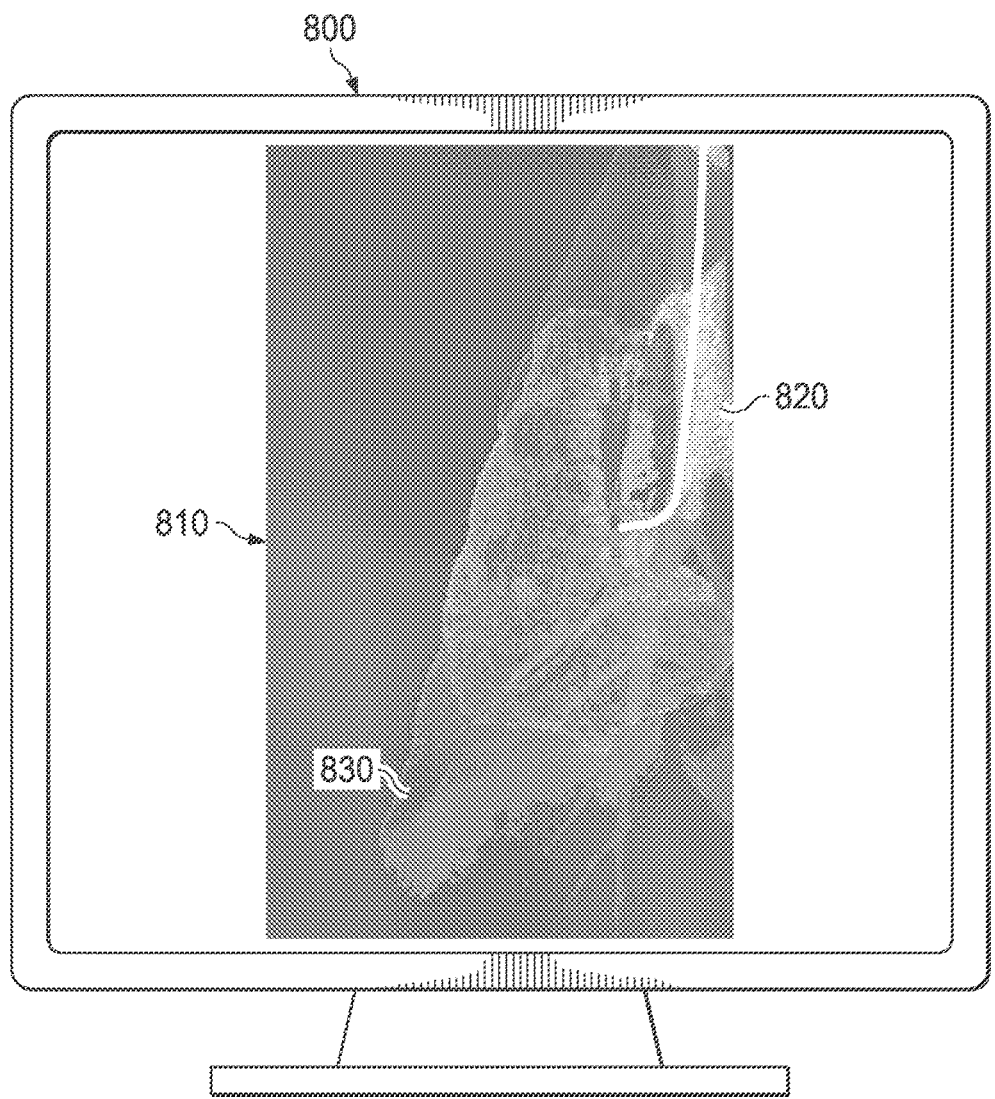

FIG. 11 is a display device on which is displayed an anatomic model image registered and overlaid on a fluoroscopic image according to an embodiment of the present disclosure.

FIG. 12 illustrates a correlation table describing correlated anatomic landmarks between fluoroscopic and anatomic frames of reference.

Figure 13A:
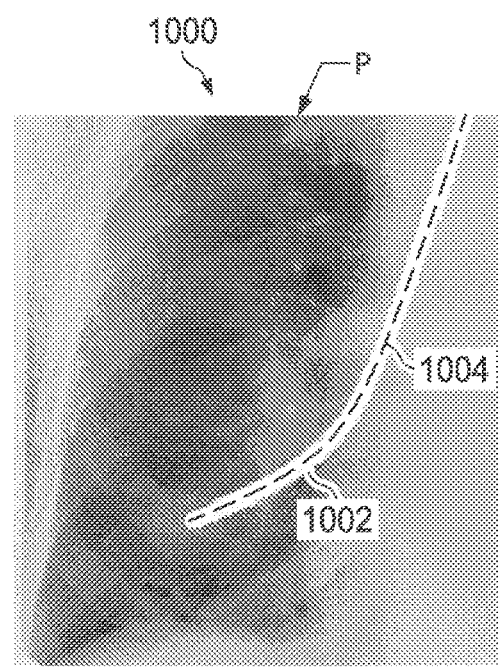
Figure 13B:
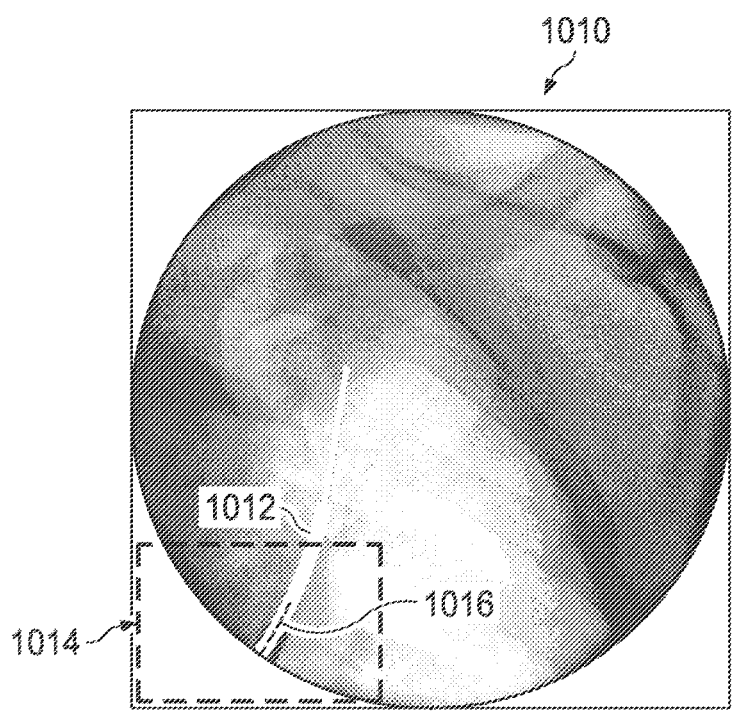

FIGS. 13A and 13B illustrate segmentation of fluoroscopic images.

Figure 14:
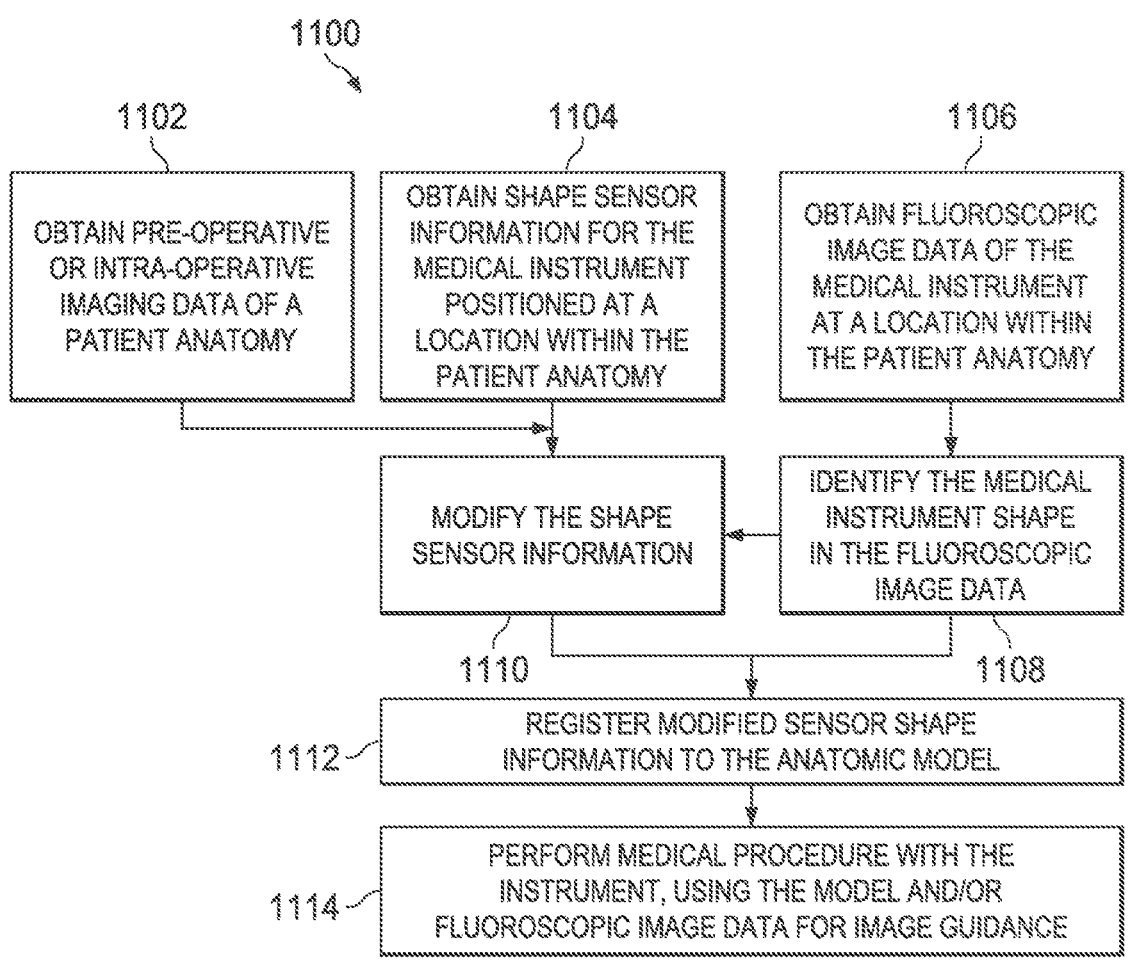

FIG. 14 illustrates a flowchart of a portion of an image-guided surgical procedure according to another embodiment of the present disclosure.

Figure 15:
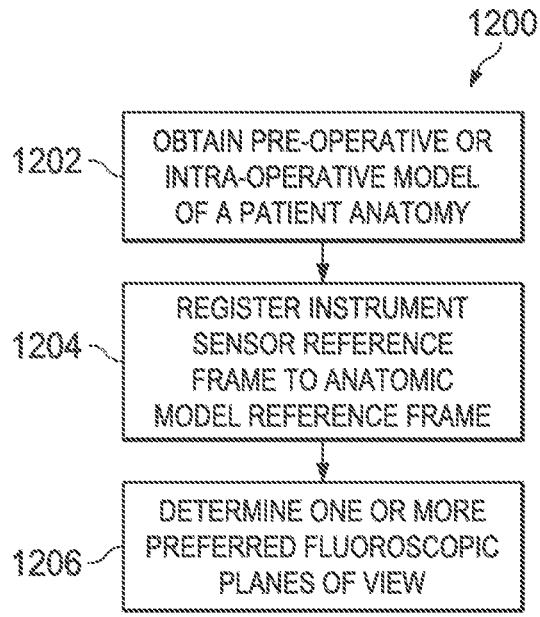

FIG. 15 illustrates a method of determining a preferred fluoroscopic plane of view.

Figure 16:
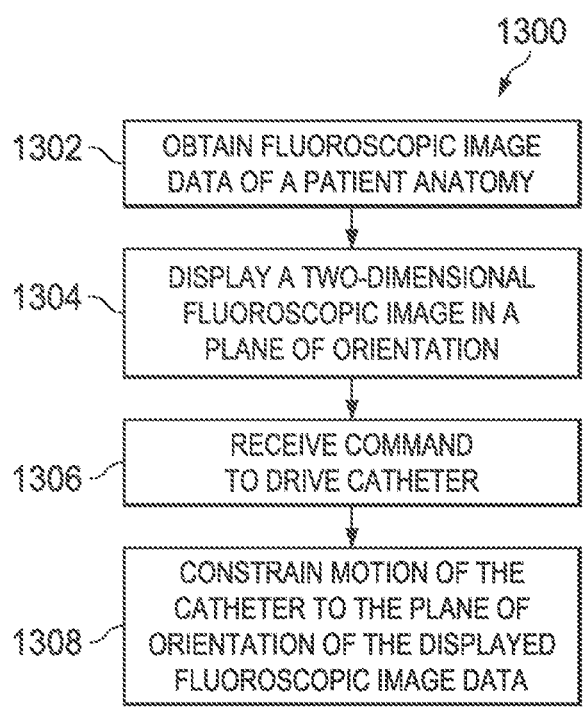

FIG. 16 illustrates a method for driving a medical instrument under two-dimensional fluoroscopic guidance.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
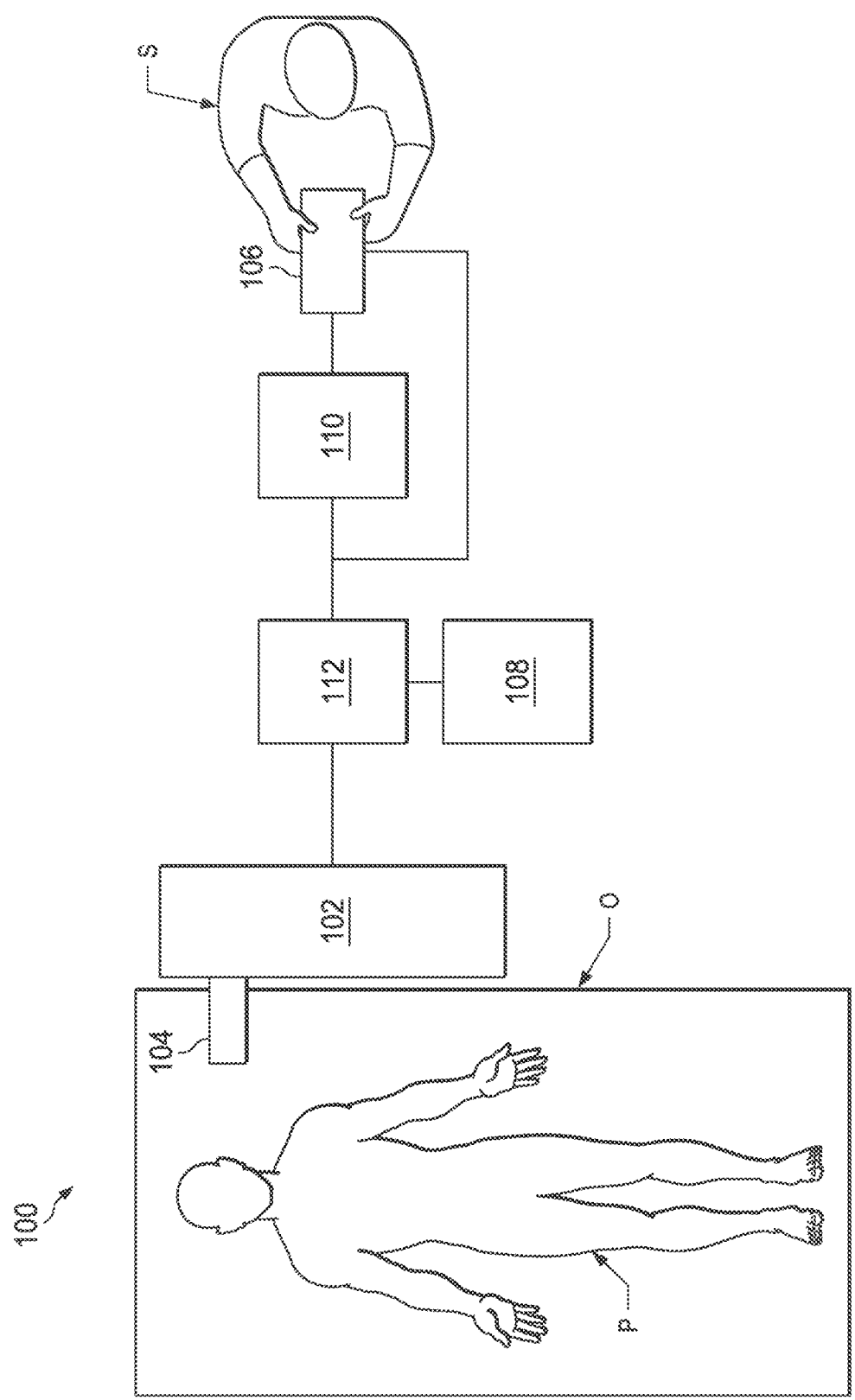
FIG. 1 is a teleoperated medical system, in accordance with embodiments of the present disclosure.

Referring to FIG. 1 of the drawings, a teleoperated medical system for use in, for example, surgical, diagnostic, therapeutic, or biopsy procedures, is generally indicated as teleoperated medical system 100. As shown in FIG. 1, the teleoperated system 100 generally includes a teleoperational manipulator assembly 102 for operating a medical instrument system 104 in performing various procedures on the patient P. The teleoperational manipulator assembly 102 may also be referred to as teleoperational assembly 102 or manipulator assembly 102. The medical instrument system 104 may also be referred to as medical instrument 104. The manipulator assembly 102 is mounted to or near an operating table O. An operator input system 106 (also called "master assembly 106") allows the clinician or surgeon S to view the interventional site and to control the manipulator assembly 102.

The operator input system 106 may be located at a surgeon's console which is usually located in the same room as operating table O. However, it should be understood that the surgeon S can be located in a different room or a completely different building from the patient P. The operator input assembly 106 generally includes one or more control devices for controlling one or more manipulator assemblies 102. The control devices may include any number of a variety of input devices, such as joysticks, trackballs, data gloves, trigger-guns, hand-operated controllers, voice recognition devices, body motion or presence sensors, or the like. In some embodiments, the control devices will be provided with the same degrees of freedom as the associated medical instruments 104 to provide the surgeon with telepresence, or the perception that the control devices are integral with the instruments 104 so that the surgeon has a strong sense of directly controlling instruments 104. In other embodiments, the control devices may have more or fewer degrees of freedom than the associated medical instruments 104 and still provide the surgeon with telepresence. In some embodiments, the control devices are manual input devices which move with six degrees of freedom, and which may also include an actuatable handle for actuating instruments (for example, for closing grasping jaws, applying an electrical potential to an electrode, delivering a medicinal treatment, or the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes a plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomic orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Motor position sensors such as resolvers, encoders, potentiometers, and other mechanisms may provide sensor data to the teleoperational assembly describing the rotation and orientation of the motor shafts. This position sensor data may be used to determine motion of the objects manipulated by the motors.

The teleoperational medical system 100 also includes a sensor system 108 with one or more sub-systems for receiving information about the instruments of the teleoperational assembly. Such sub-systems may include a position/location sensor system (e.g., an electromagnetic (EM) sensor system); a shape sensor system for determining the position, orientation, speed, velocity, pose, and/or shape of the catheter tip and/or of one or more segments along a flexible body of medical instrument system 104; and/or a visualization system for capturing images from the distal end of the catheter system.

The visualization system (e.g., visualization system 231 of FIG. 2A) may include a viewing scope assembly that records a concurrent or real-time image of the surgical site and provides the image to the clinician or surgeon S. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below). The processors of the control system 112 may execute instructions comprising instruction corresponding to processes disclosed herein.

The teleoperational medical system 100 also includes a display system 110 (also "display 110") for displaying an image or representation of the surgical site and medical instrument system(s) 104 generated by sub-systems of the sensor system 108. The display system 110 and the operator input system 106 may be oriented so the operator can control the medical instrument system 104 and the operator input system 106 with the perception of telepresence.

The display system 110 may also display an image of the surgical site and medical instruments captured by the visualization system. The display system 110 and the control devices may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display system 110 may present images of the surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may be presented as two-dimensional, three-dimensional, or four-dimensional (including e.g., time based or velocity based information) images or as images from models created from the pre-operative or intra-operative image data sets.

In some embodiments often for purposes of imaged guided surgical procedures, the display system 110 may display a virtual navigational image in which the actual location of the medical instrument 104 is registered (i.e., dynamically referenced) with the preoperative or concurrent images/model to present the clinician or surgeon S with a virtual image of the internal surgical site from the viewpoint of the location of the tip of the instrument 104. An image of the tip of the instrument 104 or other graphical or alphanumeric indicators may be superimposed on the virtual image to assist the surgeon controlling the medical instrument. Alternatively, the instrument 104 may not be visible in the virtual image.

In other embodiments, the display system 110 may display a virtual navigational image in which the actual location of the medical instrument is registered with preoperative or concurrent images to present the clinician or surgeon S with a virtual image of medical instrument within the surgical site from an external viewpoint. An image of a portion of the medical instrument or other graphical or alphanumeric indicators may be superimposed on the virtual image to assist the surgeon controlling the instrument 104.

The teleoperational medical system 100 also includes a control system 112. The control system 112 includes at least one memory and at least one computer processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein, including instructions for providing registered images to the display system 110. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104 when used in an image-guided surgical procedure. Virtual navigation using the virtual visualization system is based upon reference to the acquired preoperative or intraoperative dataset of the anatomic passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software alone or in combination with manual input is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intraoperatively at a prior time during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level (external) tracking images of the patient anatomy and virtual internal images of the patient anatomy. Various systems for using electromagnetic (EM) sensor, fiber optic sensors, or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 2A:
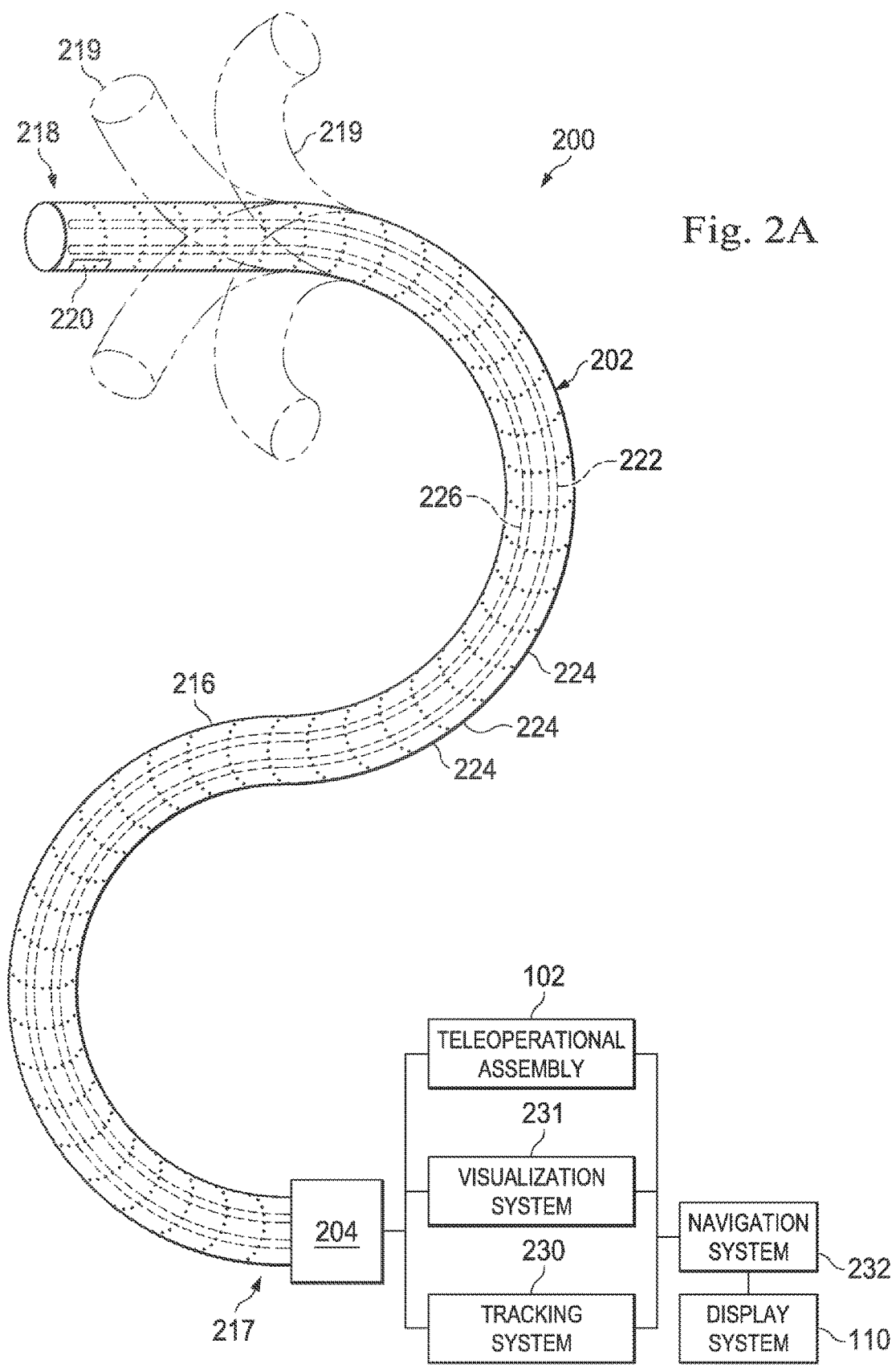
FIG. 2A illustrates a medical instrument system utilizing aspects of the present disclosure.

FIG. 2A illustrates a medical instrument system 200 system (also "medical instrument 200" or "instrument system 200"), which may be used as the medical instrument system 104 in an image-guided medical procedure performed with teleoperational medical system 100. Alternatively, the medical instrument system 200 may be used for non-teleoperational exploratory procedures or in procedures involving traditional manually operated medical instruments, such as endoscopy. Additionally or alternatively the medical instrument system 200 may be used to gather (i.e., measure) a set of data points corresponding to locations with patient anatomic passageways.

The instrument system 200 includes a catheter system 202 (also "catheter 202") coupled to an instrument body 204 that, when used to house components, may be referred to as "housing 204". The catheter system 202 includes an elongated flexible catheter body 216 having a proximal end 217 and a distal end 218 (which may be called "tip portion 218" when it is the tip portion of the catheter body 216"). In one embodiment, the flexible body 216 has an approximately 3 mm outer diameter. Other flexible body outer diameters may be larger or smaller. The catheter system 202 may optionally include a shape sensor system 222 (also "shape sensor 222") for determining the position, orientation, speed, velocity, pose, and/or shape of the catheter tip at distal end 218 and/or of one or more segments 224 along the catheter body 216. The entire length of the catheter body 216, between the distal end 218 and the proximal end 217, may be effectively divided into the segments 224. If the instrument system 200 is a medical instrument 104 of a teleoperational medical system 100, the shape sensor system 222 may be a component of the sensor system 108. If the instrument system 200 is manually operated or otherwise used for non-teleoperational procedures, the shape sensor system 222 may be coupled to a tracking system 230 that interrogates the shape sensor and processes the received shape data.

The shape sensor system 222 may include an optical fiber aligned with the flexible catheter body 216 (e.g., provided within an interior channel (not shown) or mounted externally). In one embodiment, the optical fiber has a diameter of approximately 200 µm. In other embodiments, the dimensions may be larger or smaller. The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as electromagnetic (EM) sensors, positioned along the catheter can be used for shape sensing. Alternatively, a history of data from a positional sensor, such as an EM sensor, on the instrument system during a procedure may be used to represent the shape of the instrument, particularly if an anatomic passageway is generally static. Alternatively, a wireless device with position or orientation controlled by an external magnetic field may be used for shape sensing. The history of the wireless device's position may be used to determine a shape for the navigated passageways.

The medical instrument system may, optionally, include a position sensor system 220. The position sensor system 220 may be a component of an EM sensor system with the sensor system 220 including one or more conductive coils that may be subjected to an externally generated electromagnetic field. In such an embodiment, each coil of the EM sensor system comprising the position sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, the shape sensor may also function as the position sensor because the shape of the sensor together with information about the location of the base of the shape sensor (in the fixed coordinate system of the patient) allows the location of various points along the shape sensor, including the distal tip, to be calculated.

A tracking system 230 may include the position sensor system 220 and the shape sensor system 222 for determining the position, orientation, speed, pose, and/or shape of the distal end 218 and of one or more segments 224 along the instrument system 200. The tracking system 230 may be implemented as hardware, firmware, software or a combination thereof which interact with or are otherwise executed by one or more computer processors, which may include the processors of a control system 116.

Figure 2B:
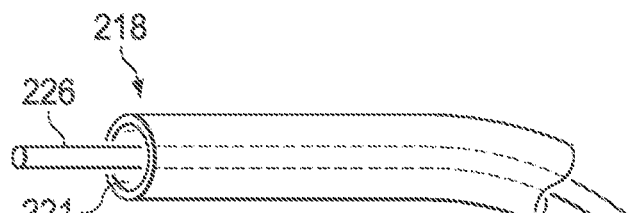
FIG. 2B illustrates a distal end of the medical instrument system of FIG. 2A with an extended medical tool, in accordance with embodiments of the present disclosure.

The flexible catheter body 216 includes a channel 221 (See FIG. 2B) sized and shaped to receive a medical instrument 226. Medical instruments may include, for example, image capture probes, biopsy instruments, laser ablation fibers, or other surgical, diagnostic, or therapeutic tools. Medical tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like.

In various embodiments, the medical instrument(s) 226 may be an image capture probe that includes a distal portion with a stereoscopic or monoscopic camera at or near the distal end 218 of the flexible catheter body 216 for capturing images (including video images) that are processed by a visualization system 231 for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

In various embodiments, the medical instrument 226 is a biopsy instrument used to remove sample tissue or a sampling of cells from a target anatomic location. The instrument 226 may be advanced from the opening of the channel 221 to perform the procedure and then retracted back into the channel when the procedure is complete. The medical instrument 226 may be removed from the proximal end 217 of the catheter flexible body or from another optional instrument port (not shown) along the flexible body.

The medical instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The instrument system 200 is also suited for navigation and treatment of other tissues, via natural or surgically created connected passageways, in any of a variety of anatomic systems, including the colon, the intestines, the kidneys, the brain, the heart, the circulatory system, and the like.

The information from the tracking system 230 may be sent to a navigation system 232 where it is combined with information from the visualization system 231 and/or the preoperatively obtained models to provide the surgeon or other operator with real-time position information on the display system 110 for use in the control of the instrument system 200. The control system 116 may utilize the position information as feedback for positioning the instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In the embodiment of FIG. 2A, the instrument system 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

In alternative embodiments, the teleoperated system may include more than one slave manipulator assembly and/or more than one master assembly. The exact number of manipulator assemblies will depend on the medical procedure and the space constraints within the operating room, among other factors. The master assemblies may be collocated, or they may be positioned in separate locations. Multiple master assemblies allow more than one operator to control one or more slave manipulator assemblies in various combinations.

Figure 3:
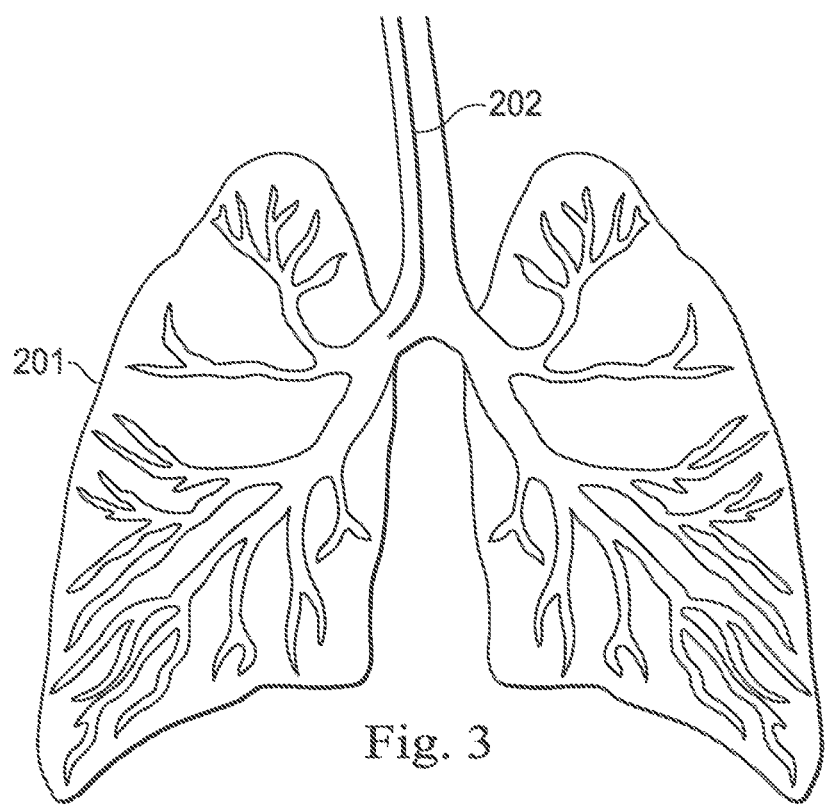
FIG. 3 illustrates the distal end of the medical instrument system of FIG. 2A positioned within a human lung.

FIG. 3 illustrates the catheter system 202 positioned within an anatomic passageway of a patient anatomy. In this embodiment, the anatomic passageway is an airway of human lungs 201. In alternative embodiments, the catheter system 202 may be used in other passageways of an anatomy.

Figure 4:
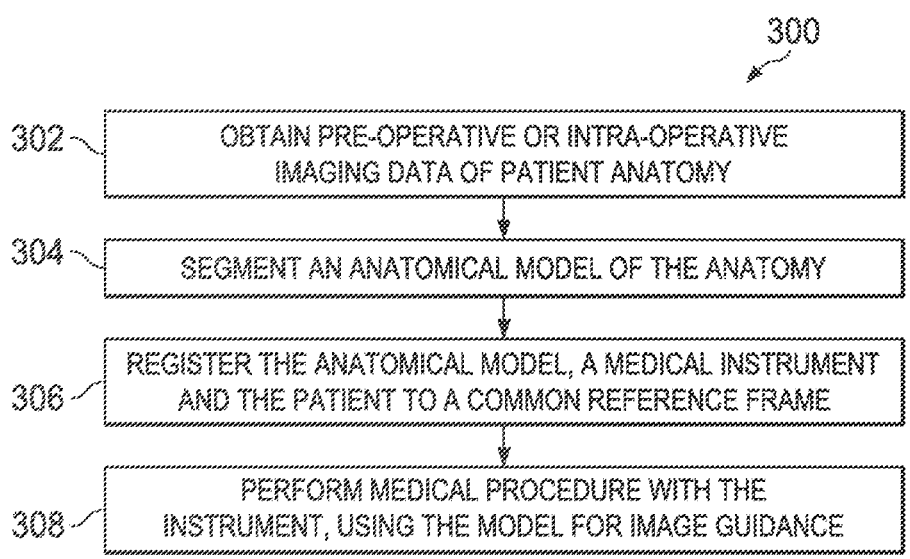
FIG. 4 is a flowchart illustrating a method used to provide guidance in an image-guided surgical procedure according to an embodiment of the present disclosure.

FIG. 4 is a flowchart illustrating a general method 300 for use in an image-guided surgical procedure. Although various provided examples describe the use of procedures performed within the anatomy, in alternative embodiments, the apparatus and methods of this disclosure need not be used within the anatomy but rather may also be used outside of the patient anatomy. At a process 302, prior image data, including pre-operative or intra-operative image data, is obtained from imaging technology such as, computed tomography (CT), magnetic resonance imaging (MRI), thermography, ultrasound, optical coherence tomography (OCT), thermal imaging, impedance imaging, laser imaging, or nanotube X-ray imaging. The pre-operative or intra-operative image data may correspond to two-dimensional, three-dimensional, or four-dimensional (including e.g., time based or velocity based information) images. For example, the image data may represent the human lungs 201 of FIG. 3.

At a process 304, computer software alone or in combination with manual input is used to convert the recorded images into a segmented two-dimensional or three-dimensional composite representation or model of a partial or an entire anatomic organ or anatomic region. The composite representation and the image data set describe the various locations and shapes of the passageways and their connectivity. More specifically, during the segmentation process the images are partitioned into segments or elements (e.g., pixels or voxels) that share certain characteristics or computed properties such as color, density, intensity, and texture. This segmentation process results in a two- or three-dimensional reconstruction that forms a model of the target anatomy or anatomic model based on the obtained image. To represent the model, the segmentation process may delineate sets of voxels representing the target anatomy and then apply a function, such as marching cube function, to generate a 3D surface that encloses the voxels. The model may be made by generating a mesh, volume, or voxel map. Additionally or alternatively, the model may include a centerline model that includes a set of interconnected line segments or points extending through the centers of the modeled passageways. Where the model includes a centerline model including a set of interconnected line segments, those line segments may be converted to a cloud or set of points. By converting the line segments, a desired quantity of points corresponding to the interconnected line segments can be selected manually or automatically.

At a process 306, the anatomic model, a medical instrument used to perform the medical procedure (e.g., instrument system 200), and the patient anatomy are co-registered in a common reference frame prior to and/or during the course of an image-guided surgical procedure on the patient. The common reference frame may be, for example, the surgical environment reference frame or the patient reference frame. The process 306 includes localizing the medical instrument with respect to the patient. The process 306 also includes registering the anatomic model with respect to the patient. Generally, registration involves the matching of measured points to points of the model through the use of rigid and/or non-rigid transforms. Measured points may be generated using landmarks in the anatomy, electromagnetic coils scanned and tracked during the procedure, or a shape sensor system. The measured points may be generated for use in an iterative closest point (ICP) technique. ICP and other registration techniques are described in U.S. Provisional Patent Application No. 62/205,440 and U.S. Provisional Patent Application No. 62/205,433, both filed Aug. 14, 2015, which are incorporated by reference herein in their entirety. At a process 308, the medical procedure may be performed using the anatomic model data to guide movement of the medical instrument.

Anatomic models created using prior image data, for example CT scans (i.e., computerized tomography scans), are used in an image guided surgical procedure to provide the fine anatomic detail suitable for many procedures. Models based on prior image data, however, are subject to registration error and do not illustrate the real-time configuration of the anatomy, including any deformation due to cyclical or non-cyclical anatomic motion, the presence of and tissue deformation due to a medical instrument, or other alterations to the patient anatomy that may have occurred since the prior image data was obtained. Fluoroscopy is a perspective imaging modality that obtains real-time moving images of a patient anatomy using X-rays. A conventional radiograph is an X-ray image obtained by placing a part of the patient in front of an X-ray detector and then illuminating it with a short X-ray pulse. In a similar fashion, fluoroscopy uses X-rays to obtain real-time moving images of the interior of the patient, including radiopaque medical instruments, radiopaque dye, and/or radiopaque fiducial markers within the surgical environment. Fluoroscopic systems may include C-arm systems which provide positional flexibility and are capable of orbital, horizontal, and/or vertical movement via manual or automated control. Non-C-arm systems are stationary and provide less flexibility in movement. Fluoroscopy systems generally use either an image intensifier or a flat-panel detector to generate two dimensional real-time images of a patient anatomy. Bi-planar fluoroscopy systems simultaneously capture two fluoroscopic images, each from different (often orthogonal) viewpoints. The quality and utility of X-ray images may vary depending upon the type of tissue imaged. Denser material such as bone and metal are generally more visible in X-ray images than the air-filled soft tissue of the lung. For procedures in the lungs, a CT model provides anatomical detail of airways and tumors that may be hard to discern on a fluoroscopy image, but the fluoroscopy image provide real-time visualization of the medical instrument and dense anatomical tissue. Thus, fluoroscopy images registered with anatomic model may be useful to clinicians navigating certain portions of the anatomy, such as the lungs.

Figure 5:
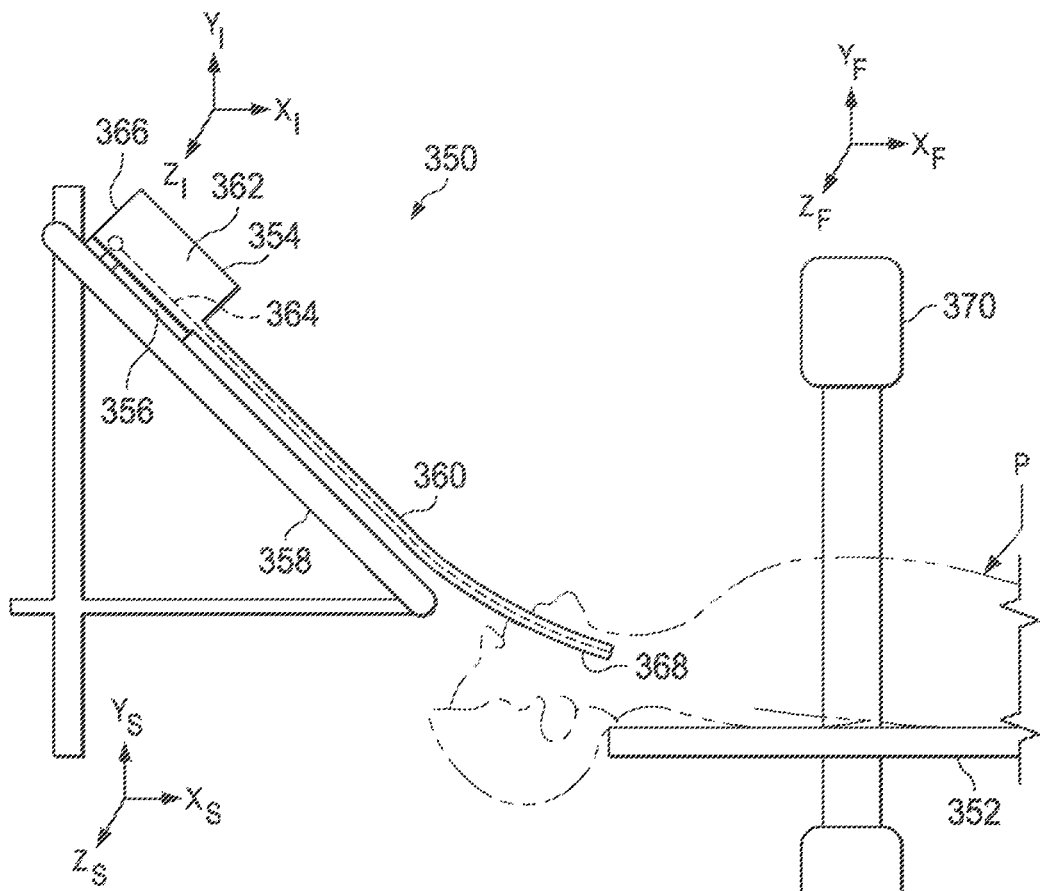
FIG. 5 is a side view of a surgical coordinate space including a medical instrument and a fluoroscopic imaging system according to an embodiment of the present disclosure.

FIG. 5 illustrates an exemplary surgical environment 350 according to some embodiments, with a surgical coordinate system XS, YS, ZS, in which a patient P is positioned on a platform 352. The patient P may be stationary within the surgical environment in the sense that gross patient movement is limited by sedation, restraint, or other means. Cyclic anatomic motion including respiration and cardiac motion of the patient P may continue, unless the patient temporarily suspends respiratory motion. Within the surgical environment 350, a medical instrument 354 is coupled to an instrument carriage 356. The instrument carriage 356 is mounted to an insertion stage 358 fixed or movable within the surgical environment 350. The instrument carriage 356 may be a component of a teleoperational manipulator assembly (e.g., manipulator assembly 102) that couples to the instrument 354 to control insertion motion (i.e. motion in an XS direction) and, optionally, motion of a distal end of the instrument in multiple directions including yaw, pitch, and roll. The instrument carriage 356 or the insertion stage 358 may include servomotors (not shown) that control motion of the instrument carriage along the insertion stage. The medical instrument 354 may include a flexible catheter 360 coupled to a proximal rigid instrument body 362. The rigid instrument body 362 is coupled and fixed relative to the instrument carriage 356. An optical fiber shape sensor 364 extends along the instrument 354 and is operable to measure a shape from a fixed or known point 366 to another point such as a portion 368 of the catheter 360. In the pictured embodiment, the portion 368 is shown as a distal end portion. In other embodiments, the portion 368 may be located elsewhere along the length of the catheter 360, including at the midportion of the catheter. The portion 368 is shaped and configured such that it may serve as an indicator portion of the catheter 360 (e.g., the portion 368 may be identified in imaging data). The medical instrument 354 may be substantially similar to the medical instrument system 200. A fluoroscopic imaging system 370 (also called a fluoroscopy system 370) is arranged near the patient P to obtain fluoroscopic images of the patient while the catheter 360 is extended within the patient. The system 370 may be, for example a mobile C-arm fluoroscopic imaging system. In some embodiments, the system 370 may be a multi-axis Artis Zeego fluoroscopic imaging system from Siemens Corporation of Washington, D.C.

Figure 6:
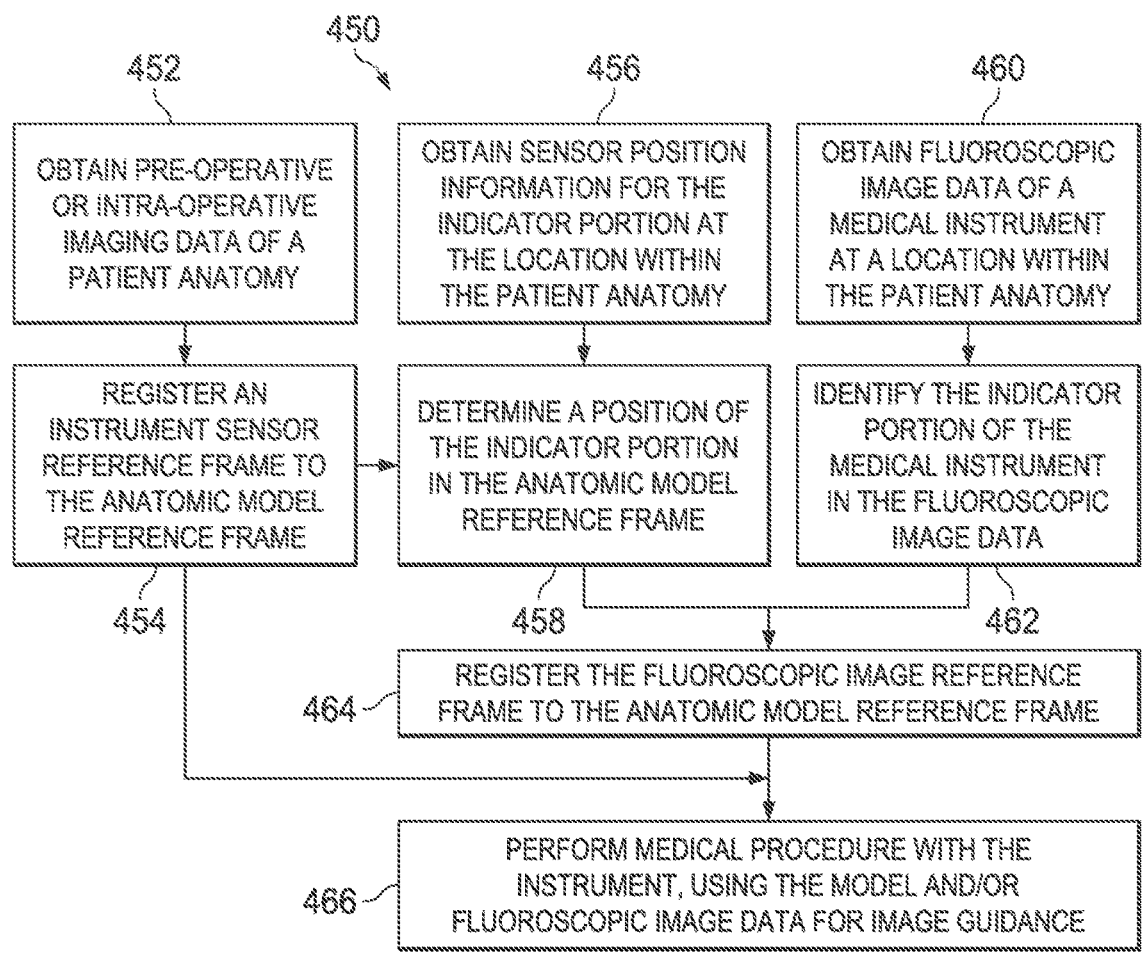
FIG. 6 illustrates a flowchart of an image-guided surgical procedure according to an embodiment of the present disclosure.

FIG. 6 is a flowchart illustrating a method 450 for performing image guided surgery in the surgical environment 350. The methods of this description, including method 450, are illustrated in FIG. 6 as a set of blocks, steps, operations, or processes. Not all of the illustrated, enumerated operations may be performed in all embodiments of the method 450. Additionally, some additional operations that are not expressly illustrated in the methods may be included before, after, in between, or as part of the enumerated processes. Some embodiments of the methods of this description include instructions that corresponded to the processes of the methods as stored in a memory. These instructions may be executed by a processor like a processor of the control system 112.

Thus, some embodiments of the method 450 may begin at a process 452, in which prior image data, including pre-operative or intra-operative image data, is obtained from imaging technology such as, CT, MRI, thermography, ultrasound, OCT, thermal imaging, impedance imaging, laser imaging, or nanotube X-ray imaging. The prior image data may correspond to two-dimensional, three-dimensional, or four-dimensional (including e.g., time based or velocity based information) images. As described above, an anatomic model is created from the prior image data in an anatomic model reference frame. At a process 454, an instrument sensor reference frame (XI, YI, ZI), which can be associated with the shape sensor 222 included in the medical instrument 200, is registered to the anatomic model reference frame (XM, YM, ZM). This registration between the model and instrument frames of reference may be achieved, for example, using a point-based ICP technique as described in incorporated by reference U.S. Provisional Pat. App. Nos. 62/205,440 and No. 62/205,433. Alternatively, the model reference frame may be registered to the sensor reference frame or the model and sensor reference frames may be registered to another common reference frame. The common reference frame may be, for example, the surgical environment reference frame (XS, YS, ZS) or a patient reference frame.

At a process 456 and with reference to FIG. 9B, sensor data (as opposed to shape information determined from imaging) is used to calculate pose information. For example, in various instances, a sensed position and orientation of a portion of the medical instrument at a location L within, near, adjacent, or outside the patient anatomy is used to determine the pose information of the medical instrument. The sensed position and orientation may be obtained, measured, or calculated from sensor data. In this embodiment, the portion 368 of the medical instrument can be referred to as an indicator portion and can comprise a radiopaque distal end portion. In other embodiments, other radiopaque portions of the medical instrument, which are visible on fluoroscopic images, may be the indicator portion. The indicator portion can include any length of the medical instrument which is visible on fluoroscopic images. The sensor information is received from the optical fiber shape sensor and is used to calculate the sensed position and orientation of the indicator portion 368 in the sensor reference frame. Based on the registration of the instrument sensor reference frame to the anatomic model reference frame (or other common reference frame) at process 454, the position and/or orientation (i.e. sensed pose) of the indicator portion in the sensor frame is translated to the anatomic model reference frame at a process 458.

At a process 460, the fluoroscopy system 370 captures fluoroscopic image data of the patient P and the catheter 360 extended within the patient. One or more of fluoroscopic images, rendered from the fluoroscopic image data, is obtained while the indicator portion 368 is positioned at or touching the anatomic location L. The images obtained while the indicator portion 368 is at the location L may be from a single viewpoint or may be a multi-planar set of images (including a set of bi-planar images) showing the indicator portion 368 from multiple viewpoints at the same time and at the same location. In some examples, the catheter 360 can be positioned outside the patient such that the indicator portion 368 is visibly adjacent the anatomic location L within the one or more fluoroscopic images.

At a process 462, the indicator portion 368 is identified in the fluoroscopic image data and thus, the position of the location L in the fluoroscopic reference frame is also identified. In various embodiments, the fluoroscopy system 370 is able to generate multi-planar images, thus providing a three-dimensional fluoroscopic reference frame (XF, YF, ZF). The use of multiple images also allows for the determination of the orientation of the indicator portion 368, thus providing pose information for the indicator portion. In other embodiments, a fluoroscopy system may provide a two-dimensional fluoroscopic reference frame.

To extract the position of the indicator portion 368 in the fluoroscopic image and thus the indicated location L in the fluoroscopic reference frame, various techniques may be used. In one embodiment, with reference to FIGS. 9A and 9B, the indicator portion 368 may be identified in the image data by comparing an image 600 in which the indicator portion 368 is not present with an image 610 in which the indicator portion 368 is present. The two images are analyzed, for example by a computer of the control system 112, to determine the graphical differences between the two images. Because the patient anatomy portion of the image is the same in the two images, the catheter 360, including the indicator portion 368 is identifiable as the structure unique to image 610. By identifying the graphical components (e.g. pixels, voxels) associated with the identified catheter 360, the presence and location of the indicator portion 368 in the fluoroscopic frame may be calculated. Because the indicator portion 368 is located at the location L, the position of the location L is also determined by the graphical analysis that extracts the indicator portion.

In another embodiment, with reference to FIGS. 9B and 9C, the indicator portion 368 may be identified in the image data by comparing an image 620 in which the indicator portion 368 is at a location K with the image 610 in which the indicator portion 368 is at location L. The two images are analyzed, for example by a computer of the control system 112, to determine the graphical differences between the two images. Because the patient anatomy portion of the image is the same in the two images, the catheter 360, including the indicator portion 368 is identifiable as the structure unique in each image 610, 620. By identifying the graphical components associated with the distal end of the identified catheter 360, the presence and location of the indicator portion 368 in the fluoroscopic frame of each image may be calculated. Because the indicator portion 368 is located at the locations L and K, the positions of locations L and K are also determined by the graphical analysis that extracts the indicator portion.

In another embodiment, with reference to FIG. 13A, the indicator portion 368 may be identified in the image data by a semi-automatic extraction technique in which a fluoroscopic image 1000 including an instrument 1002 is displayed to a user. The user uses an input device such as a touchscreen, a mouse, a trackball, or eye gaze to create an outline 1004 of the instrument 1002 or a portion of the instrument such as the distal tip. Based on the outline 1004 input received from the user, a segmentation algorithm identifies the characteristics (e.g. pixel shading, size) of the instrument 1002 in the image 1000 and proceeds to partition the segments (e.g. pixels or voxels) of the image corresponding to the instrument.

In another embodiment, with reference to FIG. 13B, the indicator portion 368 may be identified in the image data by a semi-automatic extraction technique in which a fluoroscopic image 1010 including an instrument 1022 is displayed to a user. A search area 1014 is identified by a user or may be predefined (e.g. the bottom left quadrant of the image) in which to search for an entry point 1016 of the medical instrument into the image. A segmentation algorithm may search for a predetermined shape associated with an expected shape of the medical instrument (e.g., an expected continuity or saturation of shading, an expected width, an expected length, an expected curvature). After the segmentation algorithm identifies the medical instrument in the image 1010, the algorithm proceeds to partition the segments (e.g. pixels or voxels) of the image corresponding to the instrument.

In another embodiment, an expected shape is defined by shape information received from a shape sensor and the expected shape is used to identify an initial search area for use by a semi-automatic extraction technique. The segmentation algorithm may further search for the expected shape in the initial search area to minimize time and computing resources. After the segmentation algorithm identifies the expected shape, the algorithm proceeds to partition the segments (e.g. pixels or voxels) of the image corresponding to the instrument.

In another embodiment, the indicator portion 368 may be identified by graphically analyzing and recognizing the captured fluoroscopic images for a predetermined (i.e., expected or previously known) radiopaque shape, such as the shape measured by the shape sensor or by a predetermined (i.e., expected or previously known) shape or marker at the end of the catheter. For example, a known shape of a needle extending from the catheter or a fixture at the end of the catheter may be found and extracted from the image. Graphical recognition of these indicator portions in the fluoroscopic images provides the position of the touched location L in the fluoroscopic frame.

Referring again to FIG. 6, at a process 464, the fluoroscopic image reference frame is registered to the anatomic model reference frame. Alternatively, both the fluoroscopic image reference frame and the anatomic model reference frame are registered to a common reference frame, such as the surgical reference frame. Because the process 462 provides the position and orientation of the indicator portion 368 at location L in the fluoroscopic image reference frame and the process 458 provides the position and orientation of the indicator portion 368 location L in the model reference frame, the respective frame positions of the indicator portion 368 are correlated to register the frames together. The processes 456, 458, 460, 462 may be repeated for a plurality of positions of the indicator portion at a plurality of locations in the patient anatomy. The registration at process 464 may be performed or enhanced by correlating these multiple locations in the respective frames and performing rigid or non-rigid transformations of points corresponding to the multiple locations.

At a process 466 and with reference to FIGS. 10 and 11, the registered frames of reference are displayed as the catheter traverses the patient anatomy, allowing the clinician viewing the display image(s) to utilize the benefits of real-time instrument tracking in the fluoroscopic images with the anatomic detail of the prior-time image (e.g., a CT image). FIG. 10 illustrates a display 700 displaying a fluoroscopic image 710 having a fluoroscopic reference frame (XF, YF, ZF) and a prior-time model image 720 (such as, by way of non-limiting example, a CT image acquired by CT technology or an image acquired by any other appropriate imaging technology) having model reference frame (XM, YM, ZM). The fluoroscopic reference frame and the model reference frame have been registered and the registered images are displayed side-by-side. With the reference frames registered, structures from one image may, optionally, be superimposed or overlaid on the other image to assist a clinician performing a medical procedure. For example, the catheter 360 visible in the fluoroscopic image 710 may be extracted and overlaid on the image 720. Additionally or alternatively, target tissue 730 (e.g. a tumor) visible in the image 720 may be extracted and overlaid on the fluoroscopic image 720.

FIG. 11 illustrates a display 800 displaying a single image 810 in which prior image data 820 has been overlaid on fluoroscopic image data 830. In some embodiments (not shown), a path to target tissue may be planned within the prior-time model image data and displayed within the prior-time model image (e.g., a CT image). The path may then be extracted and overlaid on the fluoroscopic image data.

Optionally, after the fluoroscopic image data is registered to the anatomic model, key features can be viewed and analyzed from two dimensional or three dimensional images generated from the fluoroscopic image data, the anatomic model, or a combination of the two. For example, a shadow in the fluoroscopic image data may indicate a tumor or may indicate where to look for the tumor in the segmented CT data used to generate the anatomic model.

Optionally, after the fluoroscopic image data is registered to the anatomic model, virtual fluoroscopic views may be generated. Because the registration indicates the fluoroscopic image plane relative to the model, a virtual view of the patient anatomy from another plane of view may be generated. For example, a virtual view from a plane orthogonal to the actual fluoroscopic image plane may be generated from the anatomic model to provide the clinician with an experience that approximates a bi-plane fluoroscopic image.

Additionally or optionally, with the fluoroscopic view registered to the anatomic model, anatomic features such as target tissue, tumors, or other landmarks may be identified in the fluoroscopic image and used to locate the corresponding feature in the anatomic model. For example, a tumor could be visible in the fluoroscopic view to help identify the corresponding tumor in the anatomic model. Once identified in the anatomic model, the tumor could be labeled as a target and a navigational path to that target could be planned within the anatomic model.

Figure 7:
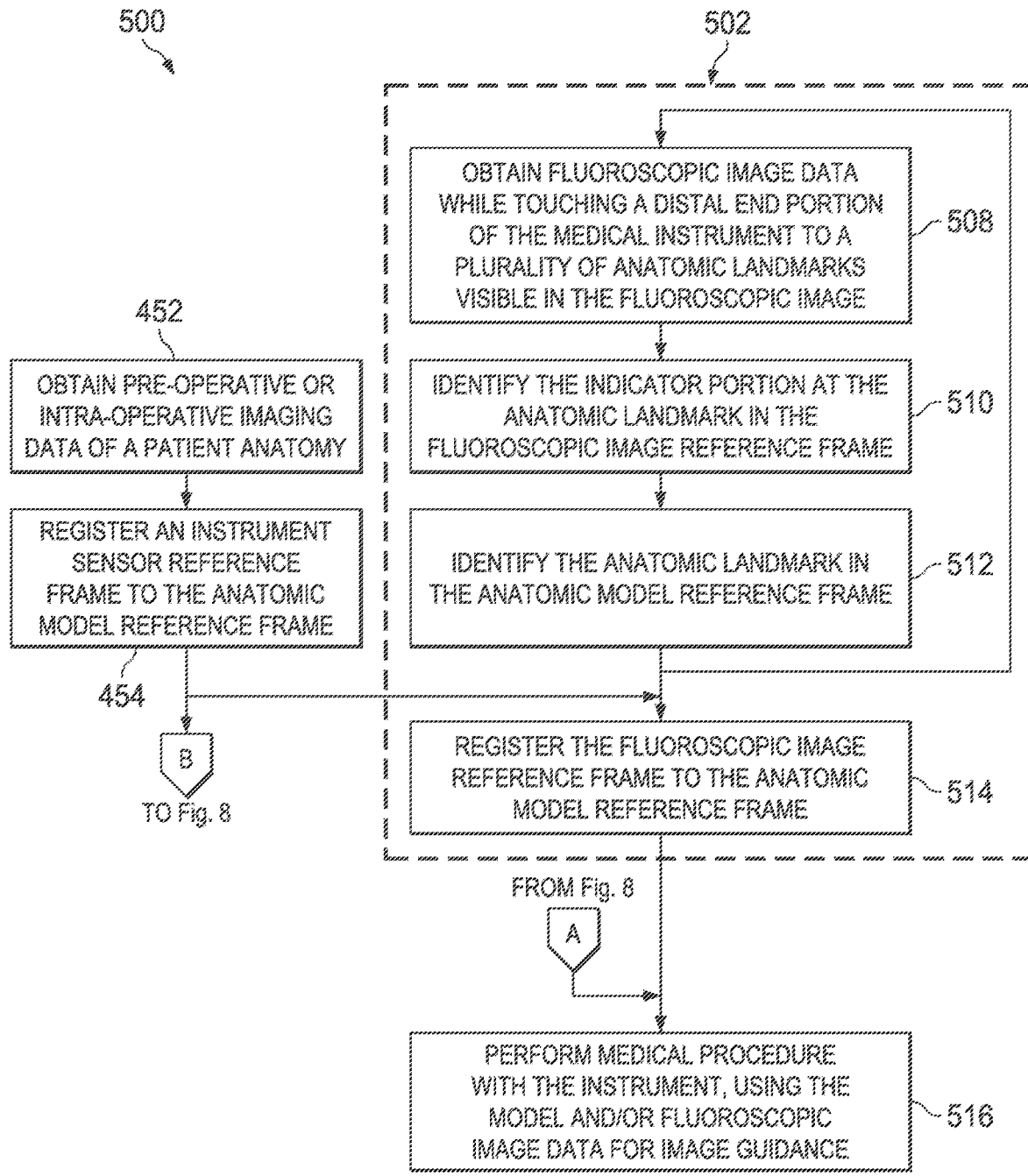
FIG. 7 illustrates a flowchart of an image-guided surgical procedure according to another embodiment of the present disclosure.

FIG. 7 is a flowchart illustrating another method 500 for performing image guided surgery in the surgical environment 350. The methods of this description, including method 500, are illustrated in FIG. 7 as a set of blocks, steps, operations, or processes. Not all of the illustrated, enumerated operations may be performed in all embodiments of the method 500. Additionally, some additional operations that are not expressly illustrated in the methods may be included before, after, in between, or as part of the enumerated processes. Some embodiments of the methods of this description include instructions that corresponded to the processes of the methods as stored in a memory. These instructions may be executed by a processor like a processor of the control system 112.

Method 500 includes the previously described process 452 of obtaining prior-time imaging data of the patient anatomy, such as a pre-operative CT scan and the process 454 of registering the instrument sensor reference frame to the anatomic model reference frame. A series of processes 502 describe a subprocess for gathering and matching anatomic landmark points and registering the fluoroscopic and model reference frames. At a process 508, the fluoroscopy system 370 captures fluoroscopic image data of the patient P and the catheter 360 while the indicator portion 368 touches or is positioned adjacent to an anatomical landmark visible in a fluoroscopic image generated from the image data. The anatomical landmark may be any unique structure visible in the fluoroscopic such as a visible portion of the spine, rib cage, sternum, collar bone, diaphragm, vasculature, or airway trec. At a process 510, the indicator portion 368 is identified in the fluoroscopic image data and thus, the position of the indicated anatomic landmark in the fluoroscopic reference frame is also identified. In various embodiments, the fluoroscopy system 370 is able to generate multi-planar images, thus providing a three-dimensional fluoroscopic reference frame (XF, YF, ZF). In other embodiments, a fluoroscopy system may provide a two-dimensional fluoroscopic reference frame. Methods for extracting the indicator portion from the fluoroscopic image data are described above. At a process 512, the same anatomic landmark is selected in anatomic model and correlated with the anatomic landmark in the fluoroscopic image data. For example, while the indicator portion of the catheter touches the anatomic landmark (as viewed by the clinician in the real-time fluoroscopic image) a user may touch a touch-screen, displaying the anatomic model, at the location of the anatomic landmark. Other marking methods for locating the anatomic landmark in the model may be used. Thus the coordinates of the anatomic landmark in the fluoroscopic reference frame and the coordinates of the anatomic landmark in the model frame of reference may become correlated. At FIG. 12, a correlation table 900 can be compiled that references each landmark 910 to a position 920 in the fluoroscopic reference frame and to a position 930 in the model reference frame. The processes 502 may be repeated for each of a plurality of anatomic landmarks. For example, three or more anatomic landmarks may be selected.

At a process 514, the fluoroscopic image reference frame is registered to the anatomic model reference frame. Anatomic landmark point registration is described in incorporated by reference U.S. Provisional Pat. App. Nos. 62/205, 440 and No. 62/205,433. For example, the set of fluoroscopic image anatomic reference points are matched with the anatomic landmark point in the model. One or both sets of matched points are then rotated, translated or otherwise manipulated by rigid or non-rigid transforms to register the fluoroscopic and model reference frames. At a process 516 and with reference to FIGS. 10 and 11, the registered frames of reference are displayed as the catheter traverses the patient anatomy, allowing the clinician viewing the display image(s) to utilize the benefits of real-time tracking instrument tracking in the fluoroscopic images with the anatomic detail of the prior-time image (e.g. CT image).

Figure 8:
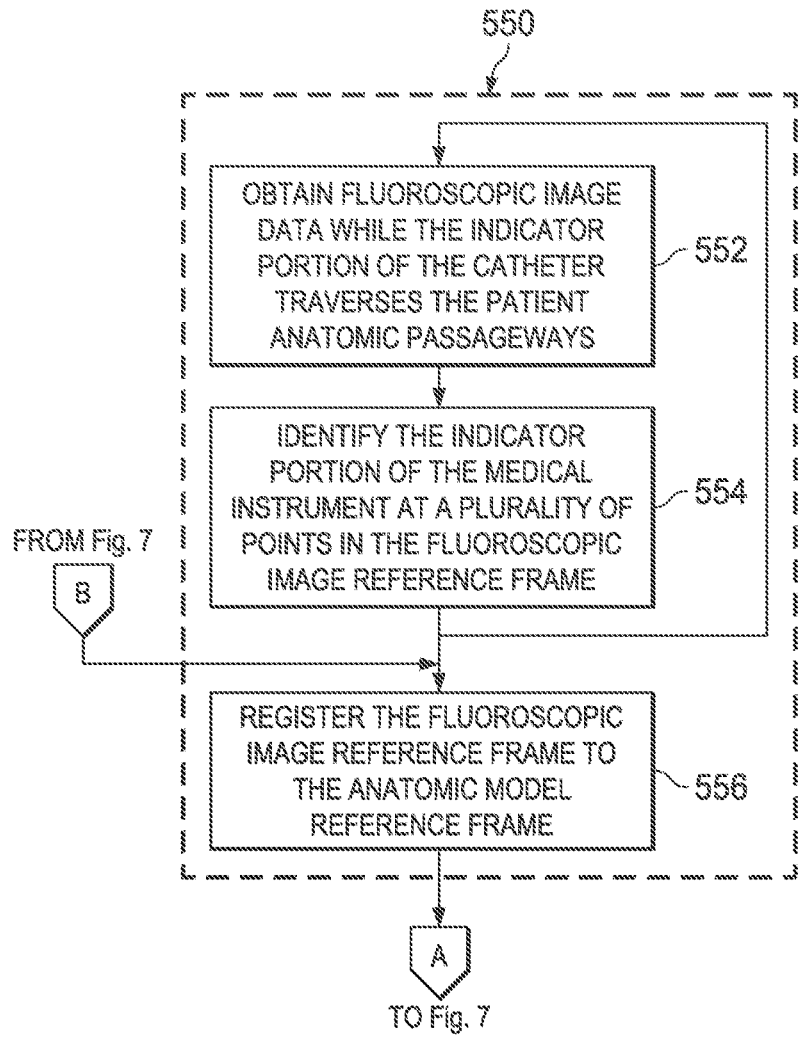
FIG. 8 illustrates a flowchart of a portion of an image-guided surgical procedure according to another embodiment of the present disclosure.

FIG. 8 is a flowchart illustrating a subprocess 550 that may be used in the method 500 to replace the process 502. At a process 552, the fluoroscopy system 370 captures fluoroscopic image data of the patient P and the catheter 360 while the indicator portion 368 traverses the patient anatomic passageways. At a process 554, a plurality of location points of the indicator portion 368 are identified in the fluoroscopic image data and thus, the positions of the location points in the fluoroscopic reference frame are also identified. In this embodiment, the fluoroscopy system 370 is able to generate multi-planar images from, thus providing a three-dimensional fluoroscopic reference frame (XF, YF, ZF). In other embodiments, a fluoroscopy system may provide a two-dimensional fluoroscopic reference frame. Methods for extracting the indicator portion from the fluoroscopic image data are described above. At a process 556, the fluoroscopic image reference frame is registered to the anatomic model reference frame. Point cloud registration is described in incorporated by reference U.S. Provisional Pat. App. Nos. 62/205,440 and No. 62/205,433. For example, the set of fluoroscopic image anatomic reference points are rotated, translated or otherwise manipulated by rigid or non-rigid transforms to match with model points in the anatomic model (e.g., model points received from a prior or concurrent CT scan of the passageways). By ICP or other point registration techniques, the fluoroscopic and model reference frames are registered.

FIG. 14 is a flowchart illustrating a method 1100 for performing image guided surgery in the surgical environment 350. The method 1100 begins at a process 1102, in which prior image data, including pre-operative or intra-operative image data, is obtained from imaging technology such as, CT, MRI, thermography, ultrasound, OCT, thermal imaging, impedance imaging, laser imaging, or nanotube X-ray imaging. The prior image data may correspond to two-dimensional, three-dimensional, or four-dimensional (including e.g., time based or velocity based information) images. As described above, an anatomic model is created from the prior image data. At a process 1104, shape sensor information is received from the medical instrument while the indicator portion of the medical instrument is positioned at a location L within the patient anatomy.

At a process 1106, the fluoroscopy system 370 captures fluoroscopic image data of the patient P and the catheter 360 extended within the patient. One or more of fluoroscopic images, rendered from the fluoroscopic image data, is obtained while the indicator portion 368 is positioned at or touching the anatomic location L. The images obtained while the indicator portion 368 is at the location L may be from a single viewpoint or may be a multi-planar set of images (including a set of bi-planar images) showing the indicator portion 368 from multiple viewpoints at the same time and at the same location.

At a process 1108, the shape of the catheter 360 is identified in the fluoroscopic image data and thus, the position of the location L (at the distal tip of the catheter) in the fluoroscopic reference frame is also identified. In various embodiments, the fluoroscopy system 370 is able to generate multi-planar images, thus providing a three-dimensional fluoroscopic reference frame (XF, YF, ZF). In other embodiments, a fluoroscopy system may provide a two-dimensional fluoroscopic reference frame. Various embodiments for extracting the shape of the catheter and/or the pose of the indicator portion are described above. At a process 1110, the shape sensor information from process 1110 is compared to the shape information determined from the fluoroscopic image data. If the shape sensor becomes twisted or sharply bent, the shape information determined from an optical fiber shape sensor may contain inaccuracies. Additionally, the error accumulates with the length of an optical fiber shape sensor, so the shape and distal tip position may be more inaccurate with longer instruments. The accuracy of the sensor information may be improved by fusing the instrument shape information received from multiple sources. At process 1110, the shape sensor information from the medical instrument is modified based upon the fluoroscopic image shape information. For example, the location of the distal tip in the shape sensor information may be adjusted to the position of the distal tip in the fluoroscopic image shape information. In another example, the shape information may be averaged or modified only along portions (e.g., the distal tip portion) where inaccuracies are expected.

At a process 1112, the modified instrument sensor information is registered to the anatomic model using any of the registration methods previously described. At a process 1114, an image guided medical procedure is performed with the medical instrument with the modified sensor information providing more accurate localization of the instrument distal tip. Based on the localized instrument distal tip, a virtual image of the patient anatomy from the perspective (position and orientation) of the distal tip may be generated from the anatomic model. Additionally, based on the localized instrument distal tip, a virtual image of the medical instrument overlaid on an image from the anatomic model may be used to guide movement of the medical instrument.

FIG. 15 illustrates a method 1200 of determining a preferred fluoroscopic plane of view. At a process 1202, prior image data, including pre-operative or intra-operative image data, is obtained from imaging technology such as, CT, MRI, thermography, ultrasound, OCT, thermal imaging, impedance imaging, laser imaging, or nanotube X-ray imaging. The prior image data may correspond to two-dimensional, three-dimensional, or four-dimensional (including e.g., time based or velocity based information) images. As described above, an anatomic model is created from the prior image data. At a process 1204, the instrument sensor 222 of medical instrument 200 is registered to the anatomic model as described above for method 450 at process 454. At a process 1206, a preferred fluoroscopic plane of view is determined to allow the clinician to visualize movement of distal tip of the catheter, movement of a biopsy needle or other tool emerging from the distal tip of the catheter, and/or a tissue area to be engaged by the tool (e.g., a tumor) or to be avoided by the tool (e.g., a lung pleura to avoid perforation). More specifically, the preferred fluoroscopic plane may be selected by determining the pose of the distal tip portion of the instrument from the shape sensor information. The preferred fluoroscopic plane may be generally parallel to the pose of the distal tip portion of the instrument (e.g., the plane of view of FIG. 13B). Additionally or alternatively, the preferred fluoroscopic plane may be determined by measuring a distance between the distal tip portion of the instrument and a tissue area of interest and determining the fluoroscopic plane of view that provides the greatest distance. This fluoroscopic plane of view may be generally parallel to the trajectory between the distal tip portion of the instrument and the tissue area, thus providing the most accurate information to clinician about whether a biopsy needle has intercepted the target tissue area or has avoided an area that would cause injury to the patient.

FIG. 16 illustrates a method 1300 for driving a medical instrument under two-dimensional fluoroscopic guidance. At a process 1302, fluoroscopic image data of a patient anatomy in a surgical reference frame is obtained from a fluoroscopy system 370. The orientation of the fluoroscopy system and thus the orientation of the plane of imaging may be determined via a variety of methods including the use of external tracking systems, imaged fiducials, or use of shape sensing data as described above for method 450. A description of the determination of the fluoroscopic plane of imaging is found in U.S. Provisional Application No. 62/216,494, covering Systems and Methods of Pose Estimation and Calibration of Perspective Imaging System in Image Guided Surgery, filed Sep. 10, 2015 which is incorporated herein by reference in its entirety. In some instances, a graphical rendering of the fluoroscopy system may be generated to facilitate obtaining a fluoroscopic image in the desired fluoroscopic image plane. In particular, such a rendering may assist the user in positioning elements of the fluoroscopy system (e.g., the fluoro arm or X-ray imager) to appropriately capture fluoroscopic images in the desired or predetermined fluoroscopic plane. In some instances, the system or user may receive a set of joint configurations for a fluoroscopy system to better achieve a system configuration for obtaining a fluoroscopic image in the desired or predetermined fluoroscopic image plane. At a process 1304, a two-dimensional fluoroscopic image is generated for display from the fluoroscopic image data. The displayed image has a plane of orientation based on the plane of orientation of the plane of imaging. At a process 1306, the control system 112 receives a command to drive movement of the catheter system 202. At a process 1308, the motion of the catheter system 202 or a portion of the catheter is constrained to the plane of plane of orientation of the displayed fluoroscopic image. In one embodiment, only the motion of the indicator portion of the catheter may be constrained to the plane of orientation of the fluoroscopic image. The motion of the indicator portion of the catheter may be constrained by limiting movement of the operator controls in a teleoperational system so that the operator is prevented from moving the controls in a direction that would move the portion of the catheter out of the plane of constraint. Additionally or alternatively, the motion of the indicator portion of the catheter may be constrained by restricting the movement of at least one actuator or actuation cable in a teleoperational manipulator assembly. Despite the constraints on the operator controls or the actuation mechanism of the instrument in the above described open loop constraint system, the indicator portion of the catheter may still experience movement of out the constrained plane due to anatomical forces from adjacent tissue. In a closed loop system, sensor information received from shape, position, or other sensors of the medical instrument may be received and analyzed by the control system to recognize movement of the indicator portion out of the plane of orientation of the fluoroscopic image. Responsive to the recognized out-of-plane movement, the control system may provide a signal or a command to adjust the indicator portion back into the plane of orientation. In some instances, the signal and/or command to adjust the indicator portion may be overridden or ignored. In other instances, the signal and/or command to adjust the indicator portion may automatically adjust the indicator portion back into the plane of orientation. In various embodiments, one or more additional fluoroscopic images may be obtained from an orthogonal or other non-parallel plane to the plane of constraint, allowing the clinician to observe any movement of the indicator portion out of the plane of constraint. In various embodiments, constraining motion of the indicator portion to the plane of orientation of the displayed fluoroscopic image may be initiated by actuation of an operator control switch which may include a manual switch, a voice-activated switch, a foot-activated switch, or other operator control mechanism. Additionally or alternatively, constraining motion of the indicator portion to the plane of orientation of the displayed fluoroscopic image may be initiated by the control system 112 in response to the display of the fluoroscopic image or recognition that the operator is viewing the fluoroscopic image.

Although this disclosure describes various systems and methods for teleoperated systems, they are also contemplated for use in non-teleoperated systems where manipulator assemblies and instruments are directly controlled. Although various provided examples describe the use of procedures performed within the anatomy, in alternative embodiments, the apparatus and methods of this disclosure need not be used within the anatomy but rather may also be used outside of the patient anatomy.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a non-transitory processor readable storage medium or device, including any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A robotic medical system comprising:
   a flexible tubular instrument with a distal portion;
   a display system; and
   one or more computer readable media with instructions for:

controlling movement of the distal portion as the instrument is advanced toward an anatomical target in a patient's anatomy;

receiving a set of intraoperative images of at least the anatomical target;

reconstructing the anatomical target in three dimensions based at least in part on the set of intraoperative images; and displaying in real time, on the display system, an additional intraoperative image of a portion of the patient's anatomy and an overlay on the additional intraoperative image indicating a location of the anatomical target based at least in part on the reconstructing.

2. The system of claim 1 wherein the additional intraoperative image is a fluoroscopic image.

3. The system of claim 1 wherein the computer readable media further includes instructions for determining a distance between a location of the distal portion and the location of the anatomical target.

4. The system of claim 1 wherein the distal portion of the flexible tubular instrument includes a channel opening for advancement of a medical instrument therethrough, and the additional intraoperative image displayed on the display system includes at least part of the medical instrument.

5. The system of claim 4 wherein the medical instrument advanced through the channel opening is a biopsy needle, and the computer readable media further includes instructions for providing information to a user on whether the biopsy needle has intercepted the location of the anatomical target.

6. The system of claim 1 wherein the distal portion of the flexible tubular instrument includes a camera, and the computer readable media includes instructions for displaying in real time, on the display system, an intraoperative image captured by the camera.

7. The system of claim 1 wherein the computer readable media further includes instructions for performing a segmentation process based at least in part on the set of intraoperative images of the anatomical target in combination with manual input from a user.

8. The system of claim 1 wherein the computer readable media further includes instructions for performing an extraction process based at least in part on the set of intraoperative images of the anatomical target.

9. A method comprising:
controlling movement of a distal portion of a flexible tubular instrument as it advances toward an anatomical target in a patient's anatomy;

receiving a set of intraoperative images of at least the anatomical target;

reconstructing the anatomical target in three dimensions based at least in part on the set of intraoperative images; and displaying in real time, on a display system, an additional intraoperative image of a portion of the patient's anatomy and an overlay on the additional intraoperative image indicating a location of the anatomical target based at least in part on the reconstructing.

10. The method of claim 9 wherein the additional intraoperative image is a fluoroscopic image.

11. The method of claim 9 further comprising determining a distance between a location of the distal portion and the location of the anatomical target.

12. The method of claim 9 wherein the distal portion of the flexible tubular instrument includes a channel opening for advancement of a medical instrument therethrough, and the additional intraoperative image displayed on the display system includes at least part of the medical instrument.

13. The method of claim 12 further comprising providing information to a user on whether the medical instrument advanced through the channel opening has intercepted the location of the anatomical target.

14. The method of claim 13 wherein the medical instrument is a biopsy needle.

15. The method of claim 9 wherein the distal portion of the flexible tubular instrument includes a camera, and the method further comprises displaying in real time, on the display system, an intraoperative image captured by the camera.

16. The method of claim 9 further comprising performing a segmentation process based at least in part on the set of intraoperative images of the anatomical target in combination with manual input from a user.

17. The method of claim 9 further comprising performing an extraction process based at least in part on the set of intraoperative images of the anatomical target.

18. A robotic medical system comprising:
a flexible tubular instrument with a distal portion including a camera and a channel opening;
a display system; and
one or more computer readable media with instructions for:
controlling movement of the distal portion as the flexible tubular instrument is advanced toward an anatomical target in a patient's anatomy;

receiving first intraoperative fluoroscopic image data of the distal portion and the anatomical target, wherein the first intraoperative fluoroscopic image data is taken from multiple viewpoints;

receiving second intraoperative fluoroscopic image data of a medical instrument advanced through the channel opening of the distal portion, wherein the second intraoperative fluoroscopic image data includes a plane of view that allows a user to visualize movement of the medical instrument; and displaying in real time, on the display system, the second intraoperative fluoroscopic image data and an overlay on the second intraoperative fluoroscopic image data indicating an intraoperative location of the anatomical target based at least in part on the first intraoperative fluoroscopic image data.

19. The system of claim 18 wherein the computer readable media further includes instructions for receiving input from the user regarding an intraoperative location of the distal portion as displayed on the display system.

20. The system of claim 18 wherein the computer readable media further includes instructions for determining an intraoperative orientation of the distal portion in a three-dimensional fluoroscopic reference frame.

21. The system of claim 18 wherein the computer readable media further includes instructions for displaying at least part of the first intraoperative fluoroscopic image data showing the anatomical target side-by-side with preoperative CT image data to help identify an intraoperative location of the anatomical target in a three-dimensional fluoroscopic reference frame.

22. The system of claim 18 wherein the computer readable media further includes instructions for determining a distance between an intraoperative location of the distal portion and the intraoperative location of the anatomical target.

23. The system of claim 18 wherein the medical instrument advanced through the channel opening is a biopsy needle, and the computer readable media further includes instructions for providing information to the user on whether the biopsy needle has intercepted the intraoperative location of the anatomical target.

24. A method comprising:
controlling movement of a distal portion of a flexible tubular instrument as it advances toward an anatomical target in a patient's anatomy, wherein the distal portion includes a camera and a channel opening;
receiving first intraoperative fluoroscopic image data of the distal portion and the anatomical target, wherein the first intraoperative fluoroscopic image data is taken from multiple viewpoints;
receiving second intraoperative fluoroscopic image data of a medical instrument advanced through the channel opening of the distal portion, wherein the second intraoperative fluoroscopic image data includes a plane of view that allows a user to visualize movement of the medical instrument; and
displaying in real time, on a display system, the second intraoperative fluoroscopic image data and an overlay on the second intraoperative fluoroscopic image data indicating an intraoperative location of the anatomical target based at least in part on the first intraoperative fluoroscopic image data.

25. The method of claim 24 further comprising receiving input from the user regarding an intraoperative location of the distal portion as displayed on the display system.

26. The method of claim 24 further comprising determining an intraoperative orientation of the distal portion in a three-dimensional fluoroscopic reference frame.

27. The method of claim 24 further comprising displaying at least part of the first intraoperative fluoroscopic image data showing the anatomical target side-by-side with preoperative CT image data to help identify an intraoperative location of the anatomical target in a three-dimensional fluoroscopic reference frame.

28. The method of claim 24 further comprising determining a distance between an intraoperative location of the distal portion and the intraoperative location of the anatomical target.

29. The method of claim 24 further comprising providing information to the user on whether the medical instrument advanced through the channel opening has intercepted the intraoperative location of the anatomical target.

30. The method of claim 29 wherein the medical instrument is a biopsy needle.

\* \* \* \* \*